US007572438B2

(12) United States Patent
Erbs et al.

(10) Patent No.: US 7,572,438 B2
(45) Date of Patent: Aug. 11, 2009

(54) MUTANT HAVING URACIL PHOSPHORIBOSYL TRANSFERASE ACTIVITY

(75) Inventors: Philippe Erbs, Strasbourg (FR); Richard Jund, Strasbourg (FR)

(73) Assignee: Transgene S.A., Strasbourg (FR)

( * ) Notice: Subject to any disclaimer, the term of this patent is extended or adjusted under 35 U.S.C. 154(b) by 0 days.

(21) Appl. No.: 11/261,561

(22) Filed: Oct. 31, 2005

(65) Prior Publication Data

US 2006/0110363 A1    May 25, 2006

Related U.S. Application Data

(60) Continuation of application No. 10/437,037, filed on May 14, 2003, now Pat. No. 7,049,117, which is a division of application No. 09/446,084, filed as application No. PCT/FR99/00904 on Apr. 16, 1999, now Pat. No. 6,596,533.

(30) Foreign Application Priority Data

Apr. 17, 1998  (FR)  .................................. 98 05054

(51) Int. Cl.
*A61K 48/00*  (2006.01)
*A01N 65/00*  (2006.01)
*A61K 31/70*  (2006.01)
*C12N 5/00*  (2006.01)
*C12N 15/00*  (2006.01)

(52) U.S. Cl. ........................ 424/93.2; 424/93.1; 514/44; 435/320.1; 435/325; 435/455

(58) Field of Classification Search ........................ None
See application file for complete search history.

(56) References Cited

U.S. PATENT DOCUMENTS

| 5,856,153 A | 1/1999 | Tiraby et al. |
| 6,066,624 A | 5/2000 | Woo et al. |

FOREIGN PATENT DOCUMENTS

WO    96/16183    5/1996

OTHER PUBLICATIONS

Oonuma, et al. Gene therapy for intraperitoneally disseminated pancreatic cancers by *Escherichia coli* uracil phophoribosiltransferase (UPRT) gene mediated by restricted replication-competent adenoviral vectors. International Journal of Cancer, 2002. 102:51-59.*
Bourbeau, et al. Suicide gene therapy with an adenovirus expressing the fusion gene CD:UPRT in human glioblastomas: different sensitivities correlate with p53 status. The Journal of Gene Medicine, 2004. 6:1320-1332.*
Hadaczek et al (Limited efficacy of gene transfer in herpes simplex virus-thymidine kinase/ganciclover gene therapy for brain tumors. Journal of Neurosurgery, 2005 102:318-335).*
Gura (Systems for Identifying New Drugs Are Often Faulty. Science, 1997. 278:1041-1042).*
Kem, L. et al., "The FUR1 Gene of *Saccharomyces cerevisiae*: Cloning, Structure and Expression of Wild-Type and Mutant Alleles", Gene Apr. 16, 1990, 88(2), 149-57, Elsevier Science Publishers B.V. (Biomedical Division).
Martinussen et al., "Two Genes Encoding Uracil-Phosphoribosyltransferase are present in *Bacillus subtilis*," J. Bacteriol. 177 (1):271-274, Jan. 1995, Am. Soc. Of Microbiology, Wash., D.C.
GenBank Acc. No. CAB11230, "Uracil Phosphoribosyltransferase (Schizosaccharomyces Pombe)," US Natl. Library of Medicine, Bethesda, MD, Apr. 4, 2000, accessed by PTO on 04 No. 2002.
Ngo et al., "Computational Complexity, Protein Structure Prediction, and the Leventhal Paradox", In The Protein Folding Problem and Tertiary Structure Prediction, Merz et al., (eds.), Birkhauser Boston: Boston, MA, pp. 433 and 492-495; 1994.

* cited by examiner

*Primary Examiner*—Sumesh Kaushal
(74) *Attorney, Agent, or Firm*—Buchanan, Ingersoll & Rooney P.C.

(57) ABSTRACT

The invention concerns a polypeptide having a uracil phosphoribosyl transferase (UPRTase) by mutation of one or several residues of the UPRTase. The invention also concerns a nucleotide sequence coding for the UPRTase mutant, a vector for expressing the latter, a viral particle, a host cell, and a composition containing them. The invention further concerns their therapeutic use and a treatment method using them. The invention is particularly useful in the context of therapy by suicide genes, in particular, for treating proliferative and infectious diseases.

7 Claims, 4 Drawing Sheets

SEQUENCE LISTING

<160> NUMBER OF SEQ ID NOS: 8

<210> SEQ ID NO 1
<211> LENGTH: 216
<212> TYPE: PRT
<213> ORGANISM: Saccharomyces cerevisiae

<400> SEQUENCE: 1

```
Met Ala Ser Glu Pro Phe Lys Asn Val Tyr Leu Leu Pro Gln Thr Asn
 1               5                  10                  15

Gln Leu Leu Gly Leu Tyr Thr Ile Ile Arg Asn Lys Asn Thr Thr Arg
            20                  25                  30

Pro Asp Phe Ile Phe Tyr Ser Asp Arg Ile Ile Arg Leu Leu Val Glu
        35                  40                  45

Glu Gly Leu Asn His Leu Pro Val Gln Lys Gln Ile Val Glu Thr Asp
 50                  55                  60

Thr Asn Glu Asn Phe Glu Gly Val Ser Phe Met Gly Lys Ile Cys Gly
65                  70                  75                  80

Val Ser Ile Val Arg Ala Gly Glu Ser Met Glu Gln Gly Leu Arg Asp
                85                  90                  95

Cys Cys Arg Ser Val Arg Ile Gly Lys Ile Leu Ile Gln Arg Asp Glu
            100                 105                 110

Glu Thr Ala Leu Pro Lys Leu Phe Tyr Glu Lys Leu Pro Glu Asp Ile
        115                 120                 125

Ser Glu Arg Tyr Val Phe Leu Leu Asp Pro Met Leu Ala Thr Gly Gly
    130                 135                 140

Ser Ala Ile Met Ala Thr Glu Val Leu Ile Lys Arg Gly Val Lys Pro
145                 150                 155                 160

Glu Arg Ile Tyr Phe Leu Asn Leu Ile Cys Ser Lys Glu Gly Ile Glu
                165                 170                 175

Lys Tyr His Ala Ala Phe Pro Glu Val Arg Ile Val Thr Gly Ala Leu
            180                 185                 190

Asp Arg Gly Leu Asp Glu Asn Lys Tyr Leu Val Pro Gly Leu Gly Asp
        195                 200                 205

Phe Gly Asp Arg Tyr Tyr Cys Val
    210                 215
```

<210> SEQ ID NO 2
<211> LENGTH: 373
<212> TYPE: PRT
<213> ORGANISM: Saccharomyces cerevisiae

<400> SEQUENCE: 2

```
Met Val Thr Gly Gly Met Ala Ser Lys Trp Asp Gln Lys Gly Met Asp
 1               5                  10                  15

Ile Ala Tyr Glu Glu Ala Ala Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
 50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Val Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Ile Met Lys Gln Phe
    130                 135                 140
```

Ile Asp Glu Arg Pro Gln Asp Trp Phe Glu Asp Ile Gly Glu Ala Ser
145                 150                 155                 160

Glu Pro Phe Lys Asn Val Tyr Leu Leu Pro Gln Thr Asn Gln Leu Leu
            165                 170                 175

Gly Leu Tyr Thr Ile Ile Arg Asn Lys Asn Thr Thr Arg Pro Asp Phe
            180                 185                 190

Ile Phe Tyr Ser Asp Arg Ile Ile Arg Leu Leu Val Glu Glu Gly Leu
            195                 200                 205

Asn His Leu Pro Val Gln Lys Gln Ile Val Glu Thr Asp Thr Asn Glu
    210                 215                 220

Asn Phe Glu Gly Val Ser Phe Met Gly Lys Ile Cys Gly Val Ser Ile
225                 230                 235                 240

Val Arg Ala Gly Glu Ser Met Glu Gln Gly Leu Arg Asp Cys Cys Arg
                245                 250                 255

Ser Val Arg Ile Gly Lys Ile Leu Ile Gln Arg Asp Glu Glu Thr Ala
            260                 265                 270

Leu Pro Lys Leu Phe Tyr Glu Lys Leu Pro Glu Asp Ile Ser Glu Arg
            275                 280                 285

Tyr Val Phe Leu Leu Asp Pro Met Leu Ala Thr Gly Gly Ser Ala Ile
            290                 295                 300

Met Ala Thr Glu Val Leu Ile Lys Arg Gly Val Lys Pro Glu Arg Ile
305                 310                 315                 320

Tyr Phe Leu Asn Leu Ile Cys Ser Lys Glu Gly Ile Glu Lys Tyr His
                325                 330                 335

Ala Ala Phe Pro Glu Val Arg Ile Val Thr Gly Ala Leu Asp Arg Gly
                340                 345                 350

Leu Asp Glu Asn Lys Tyr Leu Val Pro Gly Leu Gly Asp Phe Gly Asp
            355                 360                 365

Arg Tyr Tyr Cys Val
    370

<210> SEQ ID NO 3
<211> LENGTH: 25
<212> TYPE: DNA
<213> ORGANISM: Saccharomyces cerevisiae

<400> SEQUENCE: 3
cgggtccatg gttgaattcg aaatg                                    25

<210> SEQ ID NO 4
<211> LENGTH: 19
<212> TYPE: DNA
<213> ORGANISM: Saccharomyces cerevisiae

<400> SEQUENCE: 4
tggtgtacgc gtgtgattt                                           19

<210> SEQ ID NO 5
<211> LENGTH: 26
<212> TYPE: DNA
<213> ORGANISM: Saccharomyces cerevisiae

<400> SEQUENCE: 5
cgaagccatg gtttgcagaa ttctag                                   26

```
<210> SEQ ID NO 6
<211> LENGTH: 25
<212> TYPE: DNA
<213> ORGANISM: Saccharomyces cerevisiae

<400> SEQUENCE: 6
gttaaaagct tcataggcca tggtg                                              25

<210> SEQ ID NO 7
<211> LENGTH: 21
<212> TYPE: DNA
<213> ORGANISM: Saccharomyces cerevisiae

<400> SEQUENCE: 7
agtagagaat tcagcacgct g                                                  21

<210> SEQ ID NO 8
<211> LENGTH: 26
<212> TYPE: DNA
<213> ORGANISM: Saccharomyces cerevisiae

<400> SEQUENCE: 8
atggttccga agcctcacca atatct                                             26
```

MUTANT HAVING URACIL PHOSPHORIBOSYL TRANSFERASE ACTIVITY

CROSS-REFERENCE TO RELATED APPLICATIONS

Figure 1:
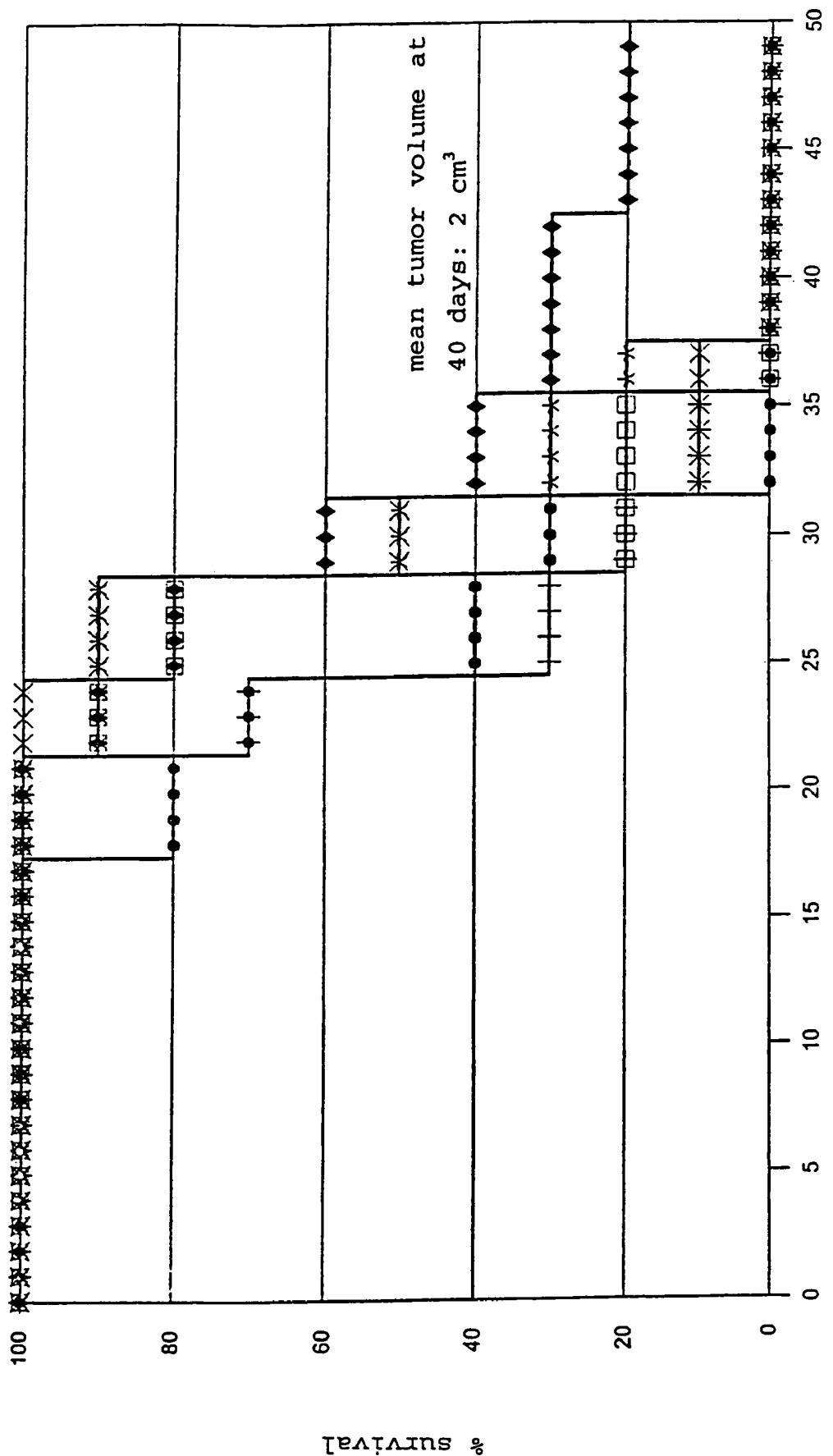

This application is a continuation of U.S. patent application Ser. No. 10/437,037, filed May 14, 2003, now U.S. Pat. No. 7,049,117, issued May 23, 2006, which is a divisional of U.S. patent application Ser. No. 09/446,084, filed on Aug. 14, 2000, now U.S. Pat. No. 6,596,533, issued Jul. 22, 2003; which is a filing under 35 U.S.C. § 371, of International Application No. PCT/FR99/00904, filed Apr. 16, 1999; and which claims priority to French Application No. 98 05054, filed on Apr. 17, 1998, respectively. These applications are hereby incorporated by reference and relied upon in their entirety.

The present invention relates to a polypeptide which possesses uracil phosphoribosyl transferase (UPRTase) activity and which is derived from a native UPRTase by one or more residues of said UPRTase being mutated. The invention also relates to a nucleotide sequence which encodes this mutant UPRTase, to a vector for expressing this latter mutant, to a viral particle and a host cell, and to a composition which comprises them. Finally, the invention is also directed towards their therapeutic use and to a method of treatment which implements them. The present invention is particularly useful, within the context of suicide gene therapy, for an application with respect, in particular, to proliferative and infectious diseases.

Gene therapy is defined as being the transfer of genetic information into a host cell or organism. The first protocol applied to man was initiated in the United States, in September 1990, on a patient who was genetically immunodeficient on account of a mutation which affected the gene encoding Adenine Deaminase (ADA). The relative success of this first experiment encouraged the development of this approach for a variety of diseases, including both genetic diseases (with the aim of correcting the malfunction of a defective gene) and acquired diseases (cancers, infectious diseases, such as AIDS, etc.). This technology has experienced a large number of developments since then, including "suicide gene" therapy, which uses genes whose expression products are able to transform an inactive substance (prodrug) into a cytotoxic substance, thereby giving rise to cell death. In 1992, several groups demonstrated the relevance of this novel approach for treating tumors and inhibiting dissemination of the HIV virus, which is responsible for AIDS.

In this respect, the gene encoding the herpes simplex type 1 virus thymidine kinase (HSV-1 TK) constitutes the prototype of the suicide genes (Caruso et al., 1993, Proc. Natl. Acad. Sci. USA 90, 7024-7028; Culver et al., 1992, Science 256, 1550-1552; Ram et al., 1997, Nat. Med. 3, 1354-1361). While the TK polypeptide is not toxic as such, it catalyzes the transformation of nucleoside analogues such as acyclovir or ganciclovir (GCV). The modified nucleosides are incorporated into the DNA chains which are in the process of elongation, inhibiting cell division as a consequence. A large number of suicide gene/prodrug pairs are currently available. Those which may more specifically be mentioned are rat cytochrome p450 and cyclophosphophamide [sic] (Wei et al., 1994, Human Gene Therapy 5, 969-978), Escherichia coli (E. Coli) purine nucleoside phosphorylase and 6-methylpurine deoxyribonucleoside (Sorscher et al., 1994, Gene Therapy 1, 223-238), E. coli guanine phosphoribosyl transferase and 6-thioxanthine (Mzoz and Moolten, 1993, Human Gene Therapy 4, 589-595) and cytosine deaminase (CDase) and 5-fluorocytosine (5FC).

CDase is involved in the pyrimidine metabolic pathway by which exogenous cytosine is transformed into uracil by means of a hydrolytic deamination. While CDase activities have been demonstrated in prokaryotes and lower eukaryotes (Jund and Lacroute, 1970, J. Bacteriol. 102, 607-615; Beck et al., 1972, J. Bacteriol. 110, 219-228; De Haan et al., 1972, Antonie van Leeuwenhoek 38, 257-263; Hoeprich et al., 1974, J. Inf. Dis. 130, 112-118; .Esders and Lynn, 1985, J. Biol. Chem. 260, 3915-3922), they are not present in mammals (Koechlin et al., 1966, Biochem Pharmacol. 15, 435-446; Polak et al., 1976, Chemotherapy 22, 137-153). The Saccharomyces cerevisiae (S. cerevisiae) FCY1 and the E. coli codA genes, which respectively encode the CDase of these two organisms, are known and their sequences have been published (EP 402 108; Erbs et al., 1997, Curr. Genet. 31, 1-6; WO93/01281).

CDase also deaminates an analogue of cytosine, i.e. 5-fluorocytosine (5-FC), thereby forming 5-fluorouracil (5-FU), which is a compound which is highly cytotoxic when it is converted into 5-fluoro-UMP (5-FUMP). Cells which lack CDase activity, either because of a mutation which inactivates the gene encoding the enzyme or because they are naturally deficient in this enzyme, as are mammalian cells, are resistant to 5-FC (Jund and Lacroute, 1970, J. Bacteriol, 102, 607-615; Kilstrup et al., 1989, J. Bacteriol. 1989 171, 2124-2127). By contrast, mammalian cells into which the sequences encoding CDase activity were transferred became sensitive to 5-FC (Huber et al., 1993, Cancer Res. 53, 4619-4626; Mullen et al., 1992, Proc. Natl. Acad. Sci. USA 89, 33-37; WO 93/01281). In addition, the neighboring, untransformed cells also become sensitive to 5-FC (Huber et al., 1994, Proc. Natl. Acad. Sci. USA 91, 8302-8306). This phenomenon, which is termed a bystander effect, is due to the cells which are expressing the CDase activity secreting 5-FU, which then intoxicates the neighboring cells by straightforward diffusion across the plasma membrane. This property of 5-FU in diffusing passively represents an advantage as compared with the tk/GCV reference system, where the bystander effect requires there to be contact with the cells which are expressing tk (Mesnil et al., 1996, Proc. Natl. Acad. Sci. USA 93, 1831-1835). All the advantages which CDase offers within the context of gene therapy, in particular anticancer gene therapy, can therefore be readily understood.

However, the sensitivity to 5-FC varies a great deal depending on the cell lines employed. For example, a low degree of sensitivity is observed in human tumor cell lines PANC-1 (pancreatic carcinoma) and SK-BR-3 (breast adenocarcinoma) which have been transduced with a retrovirus expressing the E. coli coda gene (Harris et al., 1994, Gene Therapy 1, 170-175). This undesirable phenomenon could be explained by the 5-FU which is formed by the enzymic action of the CDase either not being converted, or only being converted at a low level, into cytotoxic 5-FUMP. This step, which is normally effected in mammalian cells by orotate phosphorybosyl [sic] transferase (Peters et al., 1991, Cancer 68, 1903-1909), may be absent in particular tumors and thereby render the CDase-based gene therapy inoperative.

In prokaryotes and lower eukaryotes, uracil is transformed into UMP by the action of uracil phosphoribosyl transferase (UPRTase). This enzyme also converts 5-FU into 5-FUMP. Thus, furl mutants of the yeast S. cerevisiae are resistant to high concentrations of 5-FU (10 mM) and 5-FC (10 mM) because, with there being no UPRTase activity, the 5-FU which arises from the deamination of the 5-FC by CDase is not transformed into cytotoxic 5-FUMP (Jund and Lacroute, 1970, J. Bacteriol. 102, 607-615). The upp and FUR1 genes, which encode *E. coli* and *S. cerevisiae* UPRTase, respectively, have been cloned and sequenced (Andersen et al., 1992, Eur. J. Biochem. 204, 51-56; Kern et al., 1990, Gene 88, 149-157).

In order to remedy these drawbacks, the prior art document WO-A-96/16183 recommends using a fusion protein which encodes a two-domain enzyme possessing CDase and UPRTase activities, and demonstrates in vitro that the transfer of a hybrid codA::upp or FCY1::FUR1 gene, carried by an expression plasmid, increases the sensitization of transfected B16 cells to 5-FC.

The present invention is an improvement of the earlier technique in that it uses a mutated FUR1 gene which encodes a UPRTase which is deleted in its N-terminal part. The present invention results from the observation that, after the initiating ATG codon, the FUR1 gene contains a second ATG codon encoding methionine in position 36 of the native protein.

An FUR1 gene has now been constructed which lacks 105 nucleotides at the 5' end of the coding part, thereby making it possible to synthesize a UPRTase from which the first 35 N-terminal residues have been deleted and which starts with the methionine in position 36 in the native protein. It has been shown that the expression product of the mutant gene, designated FUR1Δ105, is able to complement an *S. cerevisiae* fur1 mutant, thereby demonstrating that it is functional. Surprisingly, the truncated mutant exhibits a UPRTase activity which is greater than that of the native enzyme, as is testified by the enzyme assays which have been carried out on COS7 cells transfected with a plasmid expressing the corresponding gene (FUR1Δ105 gene as compared with the wild-type gene). Three human tumor cell lines, which were selected because of their resistance to 5-FU, were transduced with the mutant gene carried by an adenoviral vector and exhibit an increased sensitivity to 5-FU in vitro. The sensitivity to 5-FC is also increased if the cells are coinfected with adenoviruses which are respectively expressing the FCY1 and FUR1Δ105 genes, as compared with an infection with an adenovirus expressing FCY1 alone. Even more surprisingly, the fusion protein which is produced by the hybrid FCY1 ::FUR1Δ105 gene, which results from the in-frame fusion of the FCY1 and truncated FUR1 genes, retains its UPRTase activity but exhibits a CDase activity which is increased by a factor of 10 to 30 as compared with that measured using the native FCY1 product. The high CDase activity of the bifunctional protein makes it possible to form a pool of 5-FU which generates a substantial bystander effect. It is to be noted that the CDase activity of the CDase::UPRTase fusion protein of WO-A-96/16183 was not shown to be improved.

The present invention provides a more efficient mutant, thereby making it possible to increase the sensitivity of cells to 5-FC and to improve the prospects for gene therapy using suicide genes. This mutant can be used for a large number of applications, in particular anticancer and antiviral applications, and all applications which require cell death.

For this reason, the present invention relates to a polypeptide possessing a uracil phosphoribosyl transferase (UPRTase) activity, characterized in that it is derived from a native UPRTase at least by mutating one or more residues of said UPRTase.

Within the meaning of the present invention, a polypeptide possessing a UPRTase activity refers to a polypeptide which is able to convert uracil, or one of its derivatives, into a monophosphate analog, in particular 5-FU into 5-FUMP. "Mutation" is to be understood as being the addition, deletion and/or substitution of one or more residues at any site in said polypeptide.

The native UPRTase from which the polypeptide according to the invention is derived can be of any origin, in particular of prokaryotic, fungal or yeast origin. By way of illustration, the UPRTases from *E. coli* (Anderson et al., 1992, Eur. J. Biochem 204, 51-56), from *Lactococcus lactis* (Martinussen and Hammer, 1994, J. Bacteriol. 176, 6457-6463), from *Mycobacterium bovis* (Kim et al., 1997, Biochem Mol. Biol. Int 41, 1117-1124) and from *Bacillus subtilis* (Martinussen et al., 1995, J. Bacteriol. 177, 271-274), can be used within the context of the invention. However, very particular preference is given to using a yeast UPRTase, in particular that encoded by the *S. cerevisiae* FUR1 gene, whose sequence is disclosed in Kern et al. (1990, Gene 88, 149-157). By way of information, the sequences of the genes, and those of the corresponding UPRTases, can be found in the literature and in specialized databases (SWISSPROT, EMBL, Genbank, Medline, etc.).

According to one particularly advantageous embodiment, the polypeptide according to the invention is a deletion mutant of a native UPRTase. The deletion is preferably located in the N-terminal region of the original UPRTase. The deletion can be total (affecting all the residues of said N-terminal region) or partial (affecting one or more residues which may or may not be continuous in the primary structure). In a general manner, a polypeptide consists of an N-terminal part, of a central part and of a C-terminal part, with each part representing approximately one third of the molecule. For example, in the case of the *S. cerevisiae* UPRTase, which contains 251 amino acids, the N-terminal part consists of the first 83 residues, starting with the so-called initiating methionine, which is located in the first position of the native form. In the case of the *E. coli* UPRTase, the N-terminal part covers positions 1 to 69.

This preferred embodiment can of course be combined with one or more additional mutation(s) at any site in the molecule. Preferably, the additional modification(s) do not significantly affect the UPRTase enzymic properties of the polypeptide according to the invention. It is pointed out that the biological activity of the mutants can be tested, in particular using the techniques which are described in the examples which follow.

Very preferably, the polypeptide according to the invention is derived from a native UPRTase at least by deleting all or part of the N-terminal region upstream of the second ATG codon of said native UPRTase. The total deletion of the aforesaid region is preferred. For example, the UPRTase encoded by the FUR1 gene comprises a first ATG codon (initiating ATG codon) in position +1 followed by a second in position +36. Thus, it is possible to envisage deleting residues +1 to 35 within the context of the present invention, thereby giving a polypeptide which starts at the methionine which is normally found in position +36 of the native form.

A preferred polypeptide according to the invention comprises an amino acid sequence which is substantially as depicted in the SID NO: 1 sequence identifier, starting at the Met residue in position 1 and finishing at the Val residue in position 216. The term "substantially" refers to a degree of identity with said SID NO: 1 sequence which is greater than 70%, advantageously greater than 80%, preferably greater than 90% and, very preferably greater than 95%. Still more preferably, the polypeptide comprises the amino acid sequence depicted in the SID NO: 1 sequence identifier. As mentioned above, it can contain additional mutations. Substitution of the serine residue at position 2 (position 37 in the native UPRTase) with an alanine residue may in particular be mentioned.

Advantageously, the polypeptide according to the invention exhibits a UPRTase activity which is appreciably higher than that exhibited by said native UPRTase. The results which are presented in the examples which follow clearly demonstrate a more rapid and/or more efficient conversion of 5-FU into 5-FUMP, manifesting itself in a higher degree of cytotoxicity with regard to the transfected or transduced cells. Advantageously, the UPRTase activity of the polypeptide according to the invention is greater than that exhibited by the native UPRTase by a factor of from 2 to 100, preferably of from 5 to 75, and very preferably of from 10 to 50.

According to another embodiment, the polypeptide according to the invention is a fusion polypeptide in which it is fused in-frame with at least one second polypeptide. Even though the fusion can take place at any site in the first polypeptide, the N-or C-terminal ends are preferred, in particular the N-terminal end. Advantageously, the in-frame fusion uses a second polypeptide which exhibits a cytosine deaminase (CDase) activity and is derived from a native cytosine deaminase, such that the fusion polypeptide according to the invention exhibits CDase and UPRTase activities. An FCY1::FUR1 fusion (designated FCU1 below) is preferred. Such a bifunctional polypeptide makes it possible to improve the sensitivity of the target cells to 5-FC and 5-FU. "Cytosine deaminase activity" is understood as covering the deamination of cytosine or one of its analogs. Preferably, the second polypeptide according to the invention is able to metabolize 5-FC into 5-FU.

A CDase of prokaryotic or lower eukaryotic origin is used within the context of the present invention. Still more preferably, the CDase is a yeast CDase, in particular that encoded by the *Saccharomyces cerevisiae* FCY1 gene. The cloning and the sequence of the genes encoding the CDases of different origins are available in the literature and the specialized databases. For information, the sequence of the FCY1 gene is disclosed in Erbs et al. (1997, Curr. Genet. 31, 1-6). It is of course possible to use a CDase mutant which possesses a conversion ability which is comparable or superior to that of the native enzyme. The skilled person is capable of cloning the CDase sequences on the basis of the published data, of carrying out any mutations, of testing the enzymic activity of the mutant forms in an acellular or cellular system in accordance with the technique of the art, or following the protocol given below, and of fusing the polypeptides having CDase and UPRTase activity in-frame.

A preferred example is a polypeptide which comprises an amino acid sequence which is substantially as depicted in the SID NO: 2 sequence identifier, starting at the Met residue in position 1 and finishing at the Val residue in position 373. The term "substantially" is defined as before. A polypeptide which comprises the amino acid sequence as depicted in the SID NO: 2 sequence identifier is very particularly appropriate for implementing the invention.

According to an advantageous embodiment, a bifunctional polypeptide according to the invention exhibits a CDase activity which is appreciably higher than that of said native CDase. Thus, the examples which follow demonstrate that coupling the two enzymes makes it possible to increase the sensitization of the target cells to 5-FC. The factor by which the sensitization is increased is advantageously at least 2, preferably at least 5 and, very preferably, 10 or more.

In a general manner, a polypeptide according to the invention can be produced either by the conventional methods of chemical synthesis or by recombinant DNA techniques (see, for example, Maniatis et al., 1989, Laboratory Manual, Cold Spring Harbor, Laboratory Press, Cold Spring Harbor, N.Y.). For this reason, the present invention also covers a preparation process in which a nucleotide sequence encoding said polypeptide is introduced into a cell in order to generate a transformed cell, said transformed cell is cultured under conditions appropriate for enabling said polypeptide to be produced, and said polypeptide is harvested from the cell culture. The producer cell can be of any origin and, without limitation, a bacterium, a yeast or a mammalian cell, to the extent that the nucleotide sequence under consideration is either integrated into its genome or integrated into an appropriate expression vector which is able to replicate. Naturally, the nucleotide sequence is placed under the control of transcription and translation signals which enable it to be expressed in the producer cell. Expression vectors and control signals are known to the skilled person. The polypeptide can be recovered from the medium or the cells (after they have been lyzed) and subjected to conventional purification steps (by chromatography, electrophoresis, filtration, immunopurification, etc.).

The present invention also relates to a nucleotide sequence which encodes a polypeptide according to the invention. The nucleotide sequence can be a cDNA or genomic sequence or be of a mixed type. It can, where appropriate, contain one or more introns, with these being of native, heterologous (for example the intron of the rabbit β-globin gene, etc.) or synthetic origin, in order to increase expression in the host cells. As has already been pointed out, said sequence can encode a polypeptide which is derived from the native enzyme or a mutant which exhibits a comparable or superior activity. The sequences employed within the context of the present invention can be obtained by the conventional techniques of molecular biology, for example by screening libraries with specific probes, by immunoscreening expression libraries or by PCR using suitable primers, or by chemical synthesis. The mutants can be generated from the native sequences by substituting, deleting and/or adding one or more nucleotides using the techniques of site-directed mutagenesis, of PCR, of digesting with restriction and ligation enzymes, or else by chemical synthesis. The ability of the mutants and constructs to function can be verified by assaying the enzymic activity or by measuring the sensitivity of target cells to 5-FC and/or 5-FU.

The present invention also relates to a recombinant vector which carries a nucleotide sequence according to the invention which is placed under the control of the elements which are required for expressing it in a host cell. The recombinant vector, can be of plasmid or viral origin and can, where appropriate, be combined with one or more substances which improve the transfectional efficiency and/or stability of the vector. These substances are widely documented in the literature which is available to the skilled person (see, for example,. Felgner et al., 1987, Proc. West. Pharmacol. Soc. 32, 115-121; Hodgson and Solaiman,. 1996, Nature Biotechnology 14, 339-342; Remy et al., 1994, Bioconjugate Chemistry, 5, 647-654). By way of non-limiting illustration, the substances can be polymers, lipids, in particular cationic lipids, liposomes, nuclear proteins or neutral lipids. These substances can be used alone or in combination. A combination which can be envisaged is that of a recombinant plasmid vector which is combined with cationic lipids (DOGS, DC-CHOL, sperimine-chol, spermidine-chol, etc.) and neutral lipids (DOPE).

The choice of the plasmids which can be used within the context of the present invention is immense. They can be cloning vectors and/or expression vectors. In a general manner, they are known to the skilled person and, while a number of them are available commercially, it is also possible to construct them or to modify them using the techniques of genetic manipulation. Examples which may be mentioned are the plasmids which are derived from pBR322 (Gibco BRL), pUC (Gibco BRL), pBluescript (Stratagene), pREP4, pCEP4 (Invitrogene) or p Poly (Lathe et al., 1987, Gene 57, 193-201). Preferably, a plasmid which is used in the context of the present invention contains an origin of replication which ensures that replication is initiated in a producer cell and/or a host cell (for example, the ColE1 origin will be chosen for a plasmid which is intended to be produced in *E. coli* and the oriP/EBNA1 system will be chosen if it desired that the plasmid should be self-replicating in a mammalian host cell, Lupton and Levine, 1985, Mol. Cell. Biol. 5, 2533-2542; Yates et al., Nature 313, 812-815). The plasmid can additionally comprise a selection gene which enables the transfected cells to be selected or identified (complementation of an auxotrophic mutation, gene encoding resistance to an antibiotic, etc.). Naturally, the plasmid can contain additional elements which improve its maintenance and/or its stability in a given cell (cer sequence, which promotes maintenance of a plasmid in monomeric form (Summers and Sherrat, 1984, Cell 36, 1097-1103, sequences for integration into the cell genome).

With regard to a viral vector, it is possible to envisage a vector which is derived from a poxvirus (vaccinia virus, in particular MVA, canarypoxvirus, etc.), from an adenovirus from a retrovirus, from a herpesvirus, from an alphavirus, from a foamy virus or from an adenovirus-associated virus. Preference will be given to using a vector which does not replicate and does not integrate. In this respect, adenoviral vectors are very particularly suitable for implementing the present invention.

Retroviruses have the property of infecting, and in most cases integrating into, dividing cells and in this regard are particularly appropriate for use in relation to cancer. A recombinant retrovirus according to the invention generally contains the LTR sequences, an encapsidation region and the nucleotide sequence according to the invention, which is placed under the control of the retroviral LTR or of an internal promoter such as those described below. The recombinant retrovirus can be derived from a retrovirus of any origin (murine, primate, feline, human, etc.) and in particular from the MoMuLV (Moloney murine leukemia virus), MVS (Murine sarcoma virus) or Friend murine retrovirus (Fb29). It is propagated in an encapsidation cell line which is able to supply in trans the viral polypeptides gag, pol and/or env which are required for constituting a viral particle. Such cell lines are described in the literature (PA317, Psi CRIP GP+Am-12 etc.). The retroviral vector according to the invention can contain modifications, in particular in the LTRs (replacement of the promoter region with a eukaryotic promoter) or the encapsidation region (replacement with a heterologous encapsidation region, for example the VL30 type) (see French applications 94 08300 and 97 05203).

Preference will be given to using an adenoviral vector which lacks all or part of at least one region which is essential for replication and which is selected from the E1, E2, E4 and L1-L5 regions in order to avoid the vector being propagated within the host organism or the environment. A deletion of the E1 region is preferred. However, it can be combined with (an)other modification(s)/deletion(s) affecting, in particular, all or part of the E2, E4 and/or L1-L5 regions, to the extent that the defective essential functions are complemented in trans by means of a complementing cell line and/or a helper virus. In this respect, it is possible to use second-generation vectors of the state of the art (see, for example, international applications WO-A-94/28152 and WO-A-97/04119). By way of illustration, deletion of the major part of the E1 region and of the E4 transcription unit is very particularly advantageous. For the purpose of increasing the cloning capacities, the adenoviral vector can additionally lack all or part of the non-essential E3 region. According to another alternative, it is possible to make use of a minimal adenoviral vector which retains the sequences which are essential for encapsidation, namely the 5' and 3' ITRs (Inverted Terminal Repeat), and the encapsidation region. The various adenoviral vectors, and the techniques for preparing them, are known (see, for example, Graham and Prevect, 1991, in Methods in Molecular Biology, Vol 7, p 109-128; Ed: E. J. Murey, The Human Press Inc).

Furthermore, the origin of the adenoviral vector according to the invention can vary both from the point of view of the species and from the point of view of the serotype. The vector can be derived from the genome of an adenovirus of human or animal (canine, avian, bovine, murine, ovine, porcine, simian, etc.) origin or from a hybrid which comprises adenoviral genome fragments of at least two different origins. More particular mention may be made of the CAV-1 or CAV-2 adenoviruses of canine origin, of the DAV adenovirus of avian origin or of the Bad type 3 adenovirus of bovine origin (Zakharchuk et al., Arch. Virol., 1993, 128: 171-176; Spibey and Cavanagh, J. Gen. Virol. 1989, 70: 165-172; Jouvenne et al., Gene, 1987, 60: 21-28; Mittal et al., J. Gen. Virol., 1995, 76: 93-102). However, preference will be given to an adenoviral vector of human origin which is preferably derived from a serotype C adenovirus, in particular a type 2 or 5 serotype C adenovirus.

An adenoviral vector according to the present invention can be generated in vitro in *Escherichia coli* (*E. coli*) by ligation or homologous recombination (see, for example, international application WO-A-96/17070) or else by recombination in a complementing cell line.

The elements required for expression consist of all the elements which enable the nucleotide sequence to be transcribed into RNA and the mRNA to be translated into polypeptide. These elements comprise, in particular, a promoter which may be regulatable or constitutive. Naturally, the promoter is suited to the chosen vector and the host cell. Examples which may be mentioned are the eukaryotic promoters of the PGK (phosphoglycerate kinase), MT (metallothionein; McIvor et al., 1987, Mol. Cell Biol. 7, 838-848), α-1 antitrypsin, CFTR, surfactant, immunoglobulin, β-actin (Tabin et al., 1982, Mol. Cell Biol. 2, 426-436) and SRα (Takebe et al., 1988, Mol. Cell Biol. 8, 466-472) genes, the early promoter of the SV40 virus (Simian virus), the LTR of RSV (Rous sarcoma virus), the HSV-1 TK promoter, the early promoter of the CMV virus (Cytomegalovirus)., the p7.5K pH5R, pK1L, p28 and p11 promoters of the vaccinia virus, and the E1A and MLP adenoviral promoters. The promoter can also be a promoter which stimulates expression in a tumor or cancer cell. Particular mention may be made of the promoters of the MUC-1 gene, which is overexpressed in breast and prostate cancers (Chen et al., 1995, J. Clin. Invest. 96, 2775-2782), of the CEA (standing for carcinoma embryonic antigen) gene, which is overexpressed in colon cancers (Schrewe et al., 1990, Mol. Cell. Biol. 10, 2738-2748) of the tyrosinase gene, which is overexpressed in melanomas (Vile et al., 1993, Cancer Res. 53, 3860-3864), of the ERBB-2 gene, which is overexpressed in breast and pancreatic cancers (Harris et al., 1994, Gene Therapy 1, 170-175) and of the α-fetoprotein gene, which is overexpressed in liver cancers (Kanai et al., 1997, Cancer Res. 57, 461-465). The cytomegalovirus (CMV) early promoter is very particularly preferred.

The necessary elements can furthermore include additional elements which improve the expression of the nucleotide sequence according to the invention or its maintenance in the host cell. Intron sequences, secretion signal sequences, nuclear localization sequences, internal sites for the reinitiation of translation of IRES type, transcription termination polyA sequences, tripartite leaders and origins of replication may in particular be mentioned. These elements are known to the skilled person.

The recombinant vector according to the invention can also comprise one or more additional genes of interest, with it being possible for these genes to be placed under the control of the same regulatory elements (polycistronic cassette) or of independent elements. Genes which may in particular be mentioned are the genes encoding interleukins IL-2, IL-4, IL-7, IL-10 and IL-12, interferons, tumor necrosis factor (TNF), colony stimulating factors (CSF), in particular GM-CSF, and factors acting on angiogenesis (for example PAI1-, standing for plasminogen activator inhibitor). In one particular embodiment, the recombinant vector according to the invention comprises the gene of interest encoding IL-2 or encoding interferon γ (INFβ). It is also possible to envisage combining the nucleotide sequence according to the invention with other suicide genes such as the HSV-1 TK gene, the ricin gene, the cholera toxin gene, etc.

The present invention also relates to a viral particle which comprises a recombinant vector according to the invention. Such a viral particle can be generated from a viral vector using any technique which is conventional in the field of the art. The viral particle is propagated in a complementing cell which is suited to the deficiencies of the vector. With regard to an adenoviral vector, use will, for example, be made of the 293 cell line, which was established using human embryonic kidney cells and which efficiently complements the E1 function (Graham et al., 1977, J. Gen. Virol. 36, 59-72), of the A549-E1 cell line (Imler et al., 1996, Gene Therapy 3, 75-84) or of a cell line which permits double complementation (Yeh et al., 1996, J. Virol. 70, 559-565; Krougliak and Graham, 1995, Human Gene Therapy 6, 1575-1586; Wang et al., 1995 Gene Therapy 2, 775-783; international application WO 97/04119). It is also possible to employ helper viruses to at least partially complement the defective functions. A complementing cell is understood as being a cell which is able to supply in trans the early and/or late factors which are required for encapsidating the viral genome in a viral capsid in order to generate a viral particle which contains the recombinant vector. Said cell may not be able to complement all the defective functions of the vector on its own and, in this case, can be transfected/transduced with a vector/helper virus which supplies the additional functions.

The invention also relates to a process for preparing a viralparticle, in which process:
  (i) a recombinant vector according to the invention is introduced into a complementing cell which is able to complement said vector in trans, so as to obtain a transfected complementing cell,
  (ii) said transfected complementing cell is cultured under conditions which are appropriate for enabling said viral particle to be produced, and
  (iii) said viral particle is recovered from the cell culture.

While the viral particle can of course be recovered from the culture supernatant, it can also be recovered from the cells. One of the commonly employed methods consists in lysing the cells by means of consecutive freezing/thawing cycles in order to collect the virions in the lysis supernatant. The virions can then be amplified and purified using the techniques of the art, (chromatographic method, method of ultra-centrifugation, in particular through a cesium chloride gradient, etc.).

The present invention also relates to a host cell which comprises a nucleotide sequence or a recombinant vector according to the invention, or is infected with a viral particle according to the invention. For the purposes of the present invention, a host cell consists of any cell which can be transfected with a recombinant vector or can be infected with a viral particle, as defined above. A mammalian cell, in particular a human cell is very particularly suitable. The cell can comprise said vector in a form which is or is not (episome) integrated into the genome. The cell can be a primary or tumor cell of any origin, in particular an hematopoietic cell (totipotent stem cell, leukocyte, lymphocyte, monocyte or macrophage, etc.), muscle cell (satellite cell, myocyte, myoblast, smooth muscle cell, etc.), cardiac cell, pulmonary cell, tracheal cell, hepatic cell, epithelial cell or fibroblast.

The present invention also relates to a composition which comprises a polypeptide, a nucleotide sequence, a recombinant vector, a viral particle or a host cell according to the invention in combination with a pharmaceutically acceptable excipient.

The present invention also relates to a composition which comprises a polypeptide according to the invention which exhibits a UPRTase activity and another polypeptide of interest, in particular a polypeptide of the prior art which exhibits a CDase activity.

The present invention furthermore relates to a composition which comprises a polypeptide according to the invention and a polypeptide of interest which is encoded by one of the previously mentioned genes of interest. Of these polypeptides of interest, particular mention may be made of interleukins IL-2, IL-4, IL-7, IL-10 and IL-12, interferons, tumor necrosis factor (TNF), colony stimulating factors (CSF), in particular GM-CSF, and factors acting on angiogenesis (for example PAI-1, standing for plasminogen activator inhibitor). IL-2 or INFγ are very particularly envisaged.

The composition can also be based on nucleotide sequences which enable the above polypeptides to be expressed within the host cell. The nucleotide sequences may be carried by one and the same expression vector or by two independent vectors. Said composition can of course comprise viral particles which are generated from (a) viral vector(s) expressing said nucleotide sequence(s).

For this reason, the present invention also relates to a composition which comprises a nucleotide sequence according to the invention which encodes a polypeptide exhibiting a URPTase activity and a second nucleotide sequence of interest which encodes, in particular, a polypeptide exhibiting a CDase activity.

The present invention additionally relates to a composition which comprises a nucleotide sequence according to the invention and a second nucleotide sequence of interest which encodes a polypeptide selected from IL-2 and INFγ.

A composition according to the invention is more specifically intended for the preventive or curative treatment of diseases by means of gene therapy and is more specifically aimed at proliferative diseases (cancers, tumors, restenosis, etc.) and at diseases of infectious origin, in particular of viral origin (induced by hepatitis B or C viruses, HIV, herpes, retroviruses, etc.).

A composition according to the invention can be made conventionally with a view to administering it locally, parenterally or by the digestive route. In particular, a therapeutically effective quantity of the therapeutic or prophylactic agent is combined with a pharmaceutically acceptable excipient. It is possible to envisage a large number of routes of administration. Examples which may be mentioned are the intragastric, subcutaneous, intracardiac, intramuscular, intravenous, intraperitoneal, intratumor, intranasal, intrapulmonary and intratracheal routes. In the case of these three latter embodiments, it is advantageous for administration to take place by means of an aerosol or by means of instillation. The administration can take place as a single dose or as a dose which is repeated on one or more occasions after a particular time interval. The appropriate route of administration and dosage vary depending on a variety of parameters, for example the individual, the disease to be treated or the gene(s) of interest to be transferred. The preparations based on viral particles according to the invention can be formulated in the form of doses of between $10^4$ and $10^{14}$ pfu (plaque-forming units), advantageously $10^5$ and $10^{13}$ pfu, preferably $10^6$ and $10^2$ pfu. As far as the recombinant vector according to the invention is concerned, it is possible to envisage doses comprising from 0.01 to 100 mg of DNA, preferably from 0.05 to 10 mg, very particularly preferably from 0.5 to 5 mg. A composition based on polypeptides preferably comprises from 0.05 to 10 g, very particularly preferably from 0.05 to 5 g, of said polypeptide. Naturally, the doses can be adjusted by the clinician.

The formulation can also include a diluent, an adjuvant or an excipient which is acceptable from the pharmaceutical point of view, as well as solubilizing, stabilizing and preserving agents. In the case of an injectable administration, preference is given to a formulation in an aqueous, non-aqueous or isotonic solution. It can be presented as a single dose or as a multidose, in liquid or dry (powder, lyophilizate, etc.) form which can be reconstituted at the time of use using an appropriate diluent. The formulation can also comprise appropriate quantities of prodrugs.

The present invention also relates to the therapeutic or prophylactic use of a polypeptide, of a recombinant vector, of a viral particle or of a host cell according to the invention for preparing a medicament which is intended for treating the human or animal body by gene therapy or by administering protein which has been produced by the recombinant route. According to a first possibility, the medicament can be administered directly in vivo (for example by intravenous injection, into an accessible tumor, into the lungs by means of an aerosol, into the vascular system using an appropriate catheter, etc.). It is also possible to adopt the ex vivo approach, which consists in removing cells from the patient (bone marrow stem cells, peripheral blood lymphocytes, muscle cells, etc.), transfecting or infecting them in vitro in accordance with the techniques of the art and then readministering them to the patient. A preferred use consists in treating or preventing cancers, tumors and diseases which result from unwanted cell proliferation. Conceivable applications which may be mentioned are cancers of the breast, of the uterus (in particular those induced by papilloma viruses), of the prostate, of the lung, of the bladder, of the liver, of the colon, of the pancreas, of the stomach, of the esophagus, of the larynx, of the central nervous system and of the blood (lymphomas, leukemia, etc.). It can also be used in the context of cardiovascular diseases, for example in order to inhibit or retard the proliferation of the smooth muscle cells of the blood vessel wall (restenosis). Finally, in the case of infectious diseases, it is possible to conceive of the medicament being applied to AIDS.

The invention also extends to a method for treating diseases by gene therapy, characterized in that a nucleotide sequence, a recombinant vector, a viral particle or a host cell according to the invention is administered to an host organism or cell which is in need of such treatment.

When the treatment method makes use of a nucleotide sequence, a recombinant vector or a viral particle enabling a polypeptide according to the invention, which possesses a UPRTase activity, to be expressed, it can be advantageous to additionally administer a second nucleotide sequence which encodes a second polypeptide exhibiting a CDase activity, with said second nucleotide sequence being carried by said recombinant vector or viral particle or by an independent vector or viral particle. In this latter case, the UPRTase and CDase sequences can be administered simultaneously or consecutively, with the order of administration being of no importance.

According to an advantageous embodiment, the therapeutic use or the treatment method also comprises an additional step in which pharmaceutically acceptable. quantities of a prodrug, advantageously an analog of cytosine, in particular 5-FC, are administered to the host organism or cell. By way of illustration, it is possible to use a dose of from 50 to 500 mg/kg/day, with a dose of 200 mg/kg/day being preferred. Within the context of the present invention, the prodrug is administered in accordance with standard practice, with the administration taking place prior to, concomitantly with or else subsequent to the administration of the therapeutic agent according to the invention. The oral route is preferred. It is possible to administer a single dose of prodrug or doses which are repeated for a time which is sufficiently long to enable the toxic metabolite to be produced within the host organism or cell.

Furthermore, the composition or method according to the invention can be combined with one or more substances which potentiate the cytotoxic effect of the 5-FU. Mention may in particular be made of drugs which inhibit the enzymes of the pathway for the de novo biosynthesis of the pyrimidines (for example those mentioned below), drugs such as Leucovorin (Waxman et al., .1982, Eur. J. Cancer Clin. Oncol. 18, 685-692), which, in the presence of the product of the metabolism of 5-FU (5-FdUMP), increases the inhibition of thymidylate synthase, resulting in a decrease in the pool of dTMP, which is required for replication, and finally drugs such as methotrexate (Cadman et al., 1979, Science 250, 1135-1137) which, by inhibiting dihydrofolate reductase and increasing the pool of PRPP (phosphoribosylpyrophosphate), brings about an increase in the incorporation of 5-FU into the cellular RNA.

The present invention is also directed towards using the sequences or recombinant vectors according to the invention as positive selection markers in mammalian cells. Advantageously, the cells are transfected and the cell mixture is then cultured in the presence of inhibitors of the pathway for the de novo biosynthesis of pyrimidines, such as PALA (N-(phosphonoacetyl)-L-aspartate; Moore et al., 1982, Biochem. Pharmacol. 31, 3317-3321), A77 1726 (active metabolite of Leflunomide; Davis et al., 1996, Biochem. 35, 1270-1273) and Brequinar (Chen et al., 1992, Cancer Res. 52, 3251-3257). The presence of such inhibitors blocks the de novo synthesis of UMP, which is required for synthesizing RNA and DNA, thereby resulting in cell death. This cytotoxic effect can be circumvented by expressing the nucleotide sequence according to the invention encoding a UPRTase activity in the presence of uracil or by coexpressing this latter sequence with sequences encoding a CDase activity (where appropriate in fused form) in the presence of cytosine. As a consequence, only the transfected cells (cells which have incorporated the UPRTase/CDase sequences) will be able to grow in the presence of inhibitors of the pyrimidine synthesis pathway. Thus, the use according to the invention enables a transfected cell to be efficiently identified in, and/or isolated from, a cell mixture.

The present invention also relates to the use of the sequences or recombinant vectors according to the invention as negative selection markers in experiments in which the genes of embryonic stem cells, on which methods for preparing transgenic animals are based, are interrupted (knocked out) (see, for example, Capecchi, 1989, Science 244, 1288-1292; Reid et al., 1990, Proc. Natl. Acad. Sci. USA 87, 4299-4303). Such a use, in combination with the gene for resistance to neomycin, for example, can make it possible to select the cells which have undergone an homologous recombination event and which will alone be able to grow in the presence of Geneticin and the corresponding fluorinated pyrimidines (5-FU if a nucleotide sequence according to the invention is used which encodes a UPRTase activity, and 5-FC when a nucleotide sequence encoding a CDase activity is also used). The cells which have undergone a non-targeted recombination event are able to grow in the presence of Geneticin but not in the presence of the fluorinated pyrimidines. Another potential use as a negative selection marker is to be found in the plant field since, just like mammalian cells, plants do not possess any endogenous CDase activity. They can be sensitized to 5-FC by transfecting a nucleotide sequence according to the invention which enables an exogenous CDase to be expressed (see, for example, Perera et al. 1993, Plant. Mol. Biol. 23, 797-799).

EXAMPLES

Figure 2:
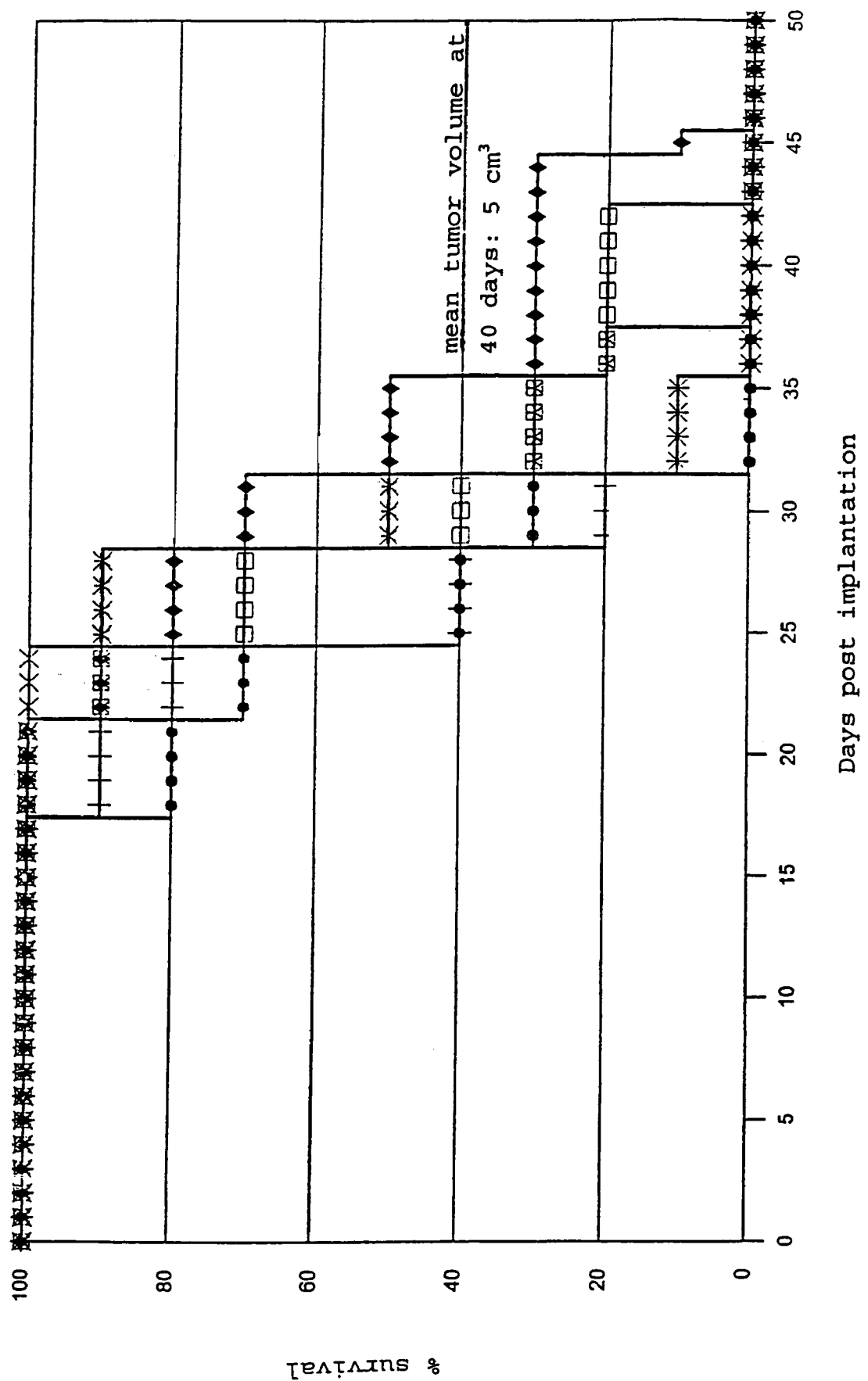
Figure 3:
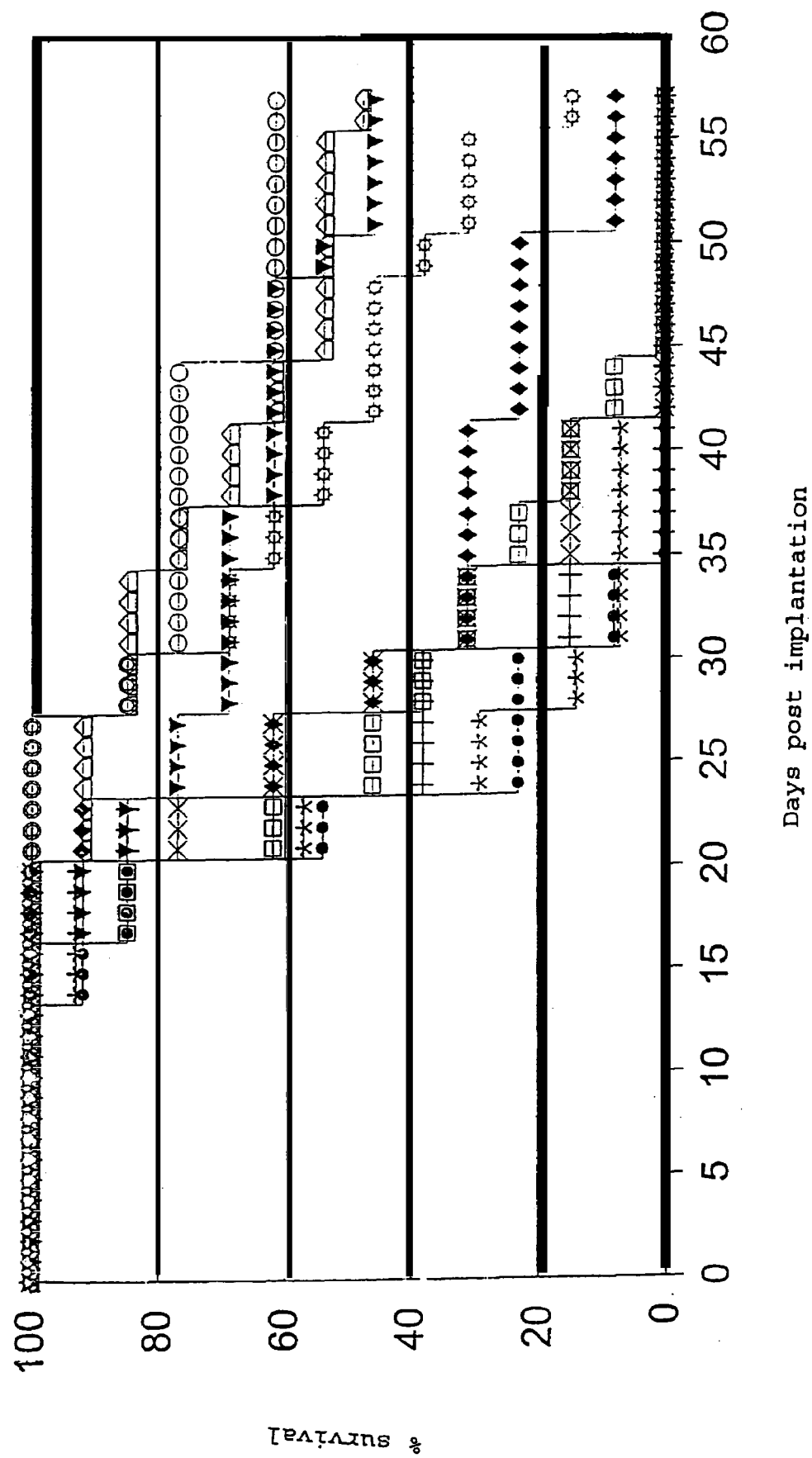
Figure 4:
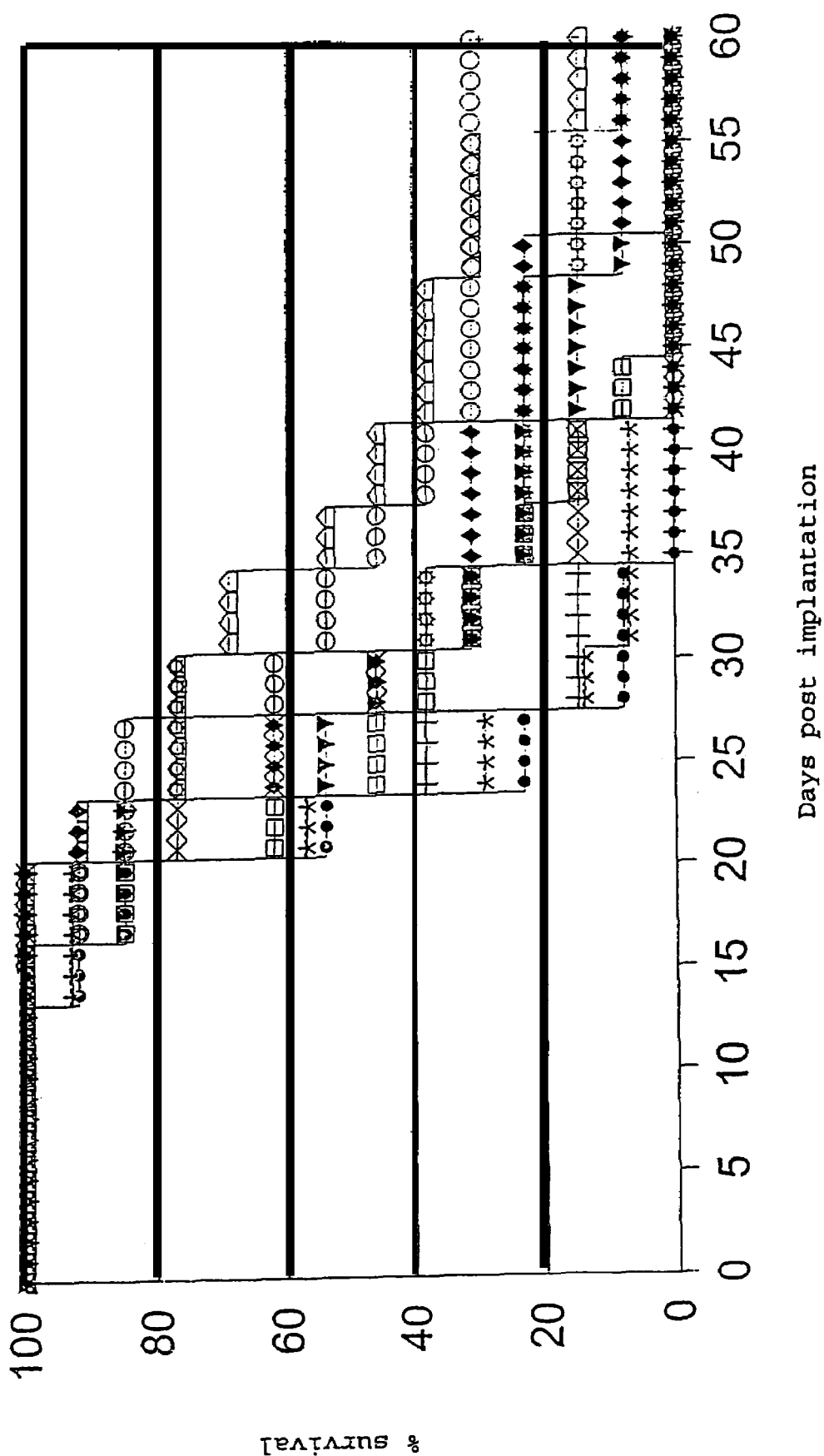

The present invention is illustrated, without for all that being limited, by the following examples in which:

FIG. 1 depicts the rate of survival of B6D2 mice which have been implanted with B16F0 tumor cells. The different groups of mice (10 mice per group) are treated with the following compositions:
● Vehicle/saline; + Vehicle/5-FC; * Ad null/saline; – Ad null/5-FC; × AdFCU1/saline; ◆ AdFCU1/5-FC FIG. 2 depicts-the rate of survival of B6D2 mice which have been implanted with B16F0 tumor cells. The different groups of mice (10 mice per group) are treated with the following compositions:
● Vehicle/saline; + Vehicle/GCV; * Ad null/saline; – Ad null/GCV; × AdTK/saline; ◆ AdTK/GCV FIG. 3 depicts the rate of survival of B6D2 mice which have been implanted with B16F0 tumor cells. The different groups of mice (13 mice per group) are treated with the following compositions:
● Vehicle/saline; + Vehicle/5-FC; * Ad null/saline; – Ad null/5-FC; × Ad null + AdFCU1/saline; ◆ Adnull + AdFCU1/5-FC; ▼ Adnull + AdmuIFNg/saline; △ Adnull + AdmuIFNg/5-FC; ○ AdmuIFNg + AdFCU1/saline; ○ AdmuIFNg + AdFCU1/5-FC FIG. 4 depicts the rate of survival of B6D2 mice which have been implanted with B16F0 tumor cells. The different groups of mice (13 mice per group) are treated with the following compositions:
● Vehicle/saline; + Vehicle/5-FC; * Ad null/saline; – Ad null/5-FC; × Adnull + AdFCU1/saline; ◆ Adnull + AdFCU1/5-FC; ▼ Adnull + AdhuIL-2/saline; △ Adnull + AdhuIL-2/5-FC; ○ AdhuIL-2 + AdFCU1/saline; ○ AdhuIL-2 + AdFCU1/5-FC The constructs described below are prepared using the general techniques of genetic engineering and molecular cloning as detailed in Maniatis et al. (1989, Laboratory Manual, Cold Spring Harbor, Laboratory Press, Cold Spring Harbor, N.Y.) or in accordance with the manufacturer's recommendations when a commercial kit is used. The homologous recombination steps are preferably carried out in the *E. coli* strain BJ 5183 (Hanahan, 1983, J. Mol. Biol. 166, 557-580). With regard to repairing the restriction sites, the technique employed consists in using the large fragment (Klenow fragment) of *E. coli* DNA polymerase I to fill in the 5' protruding ends. In addition, the adenoviral genome fragments employed in the different constructs described below are shown-precisely in accordance with their positions in the nucleotide sequence of the Ad5 genome, as disclosed in the Genebank database under reference M73260.

With regard to the cell biology, the cells are transfected or transduced and cultured in accordance with the standard techniques which are well known to the skilled person. With regard to the yeast strains, use is made of the conventional techniques which are described, in particular, in Guthrie and Fink (1991, Methods in Enzymology, Vol. 194, Guide to Yeast Genetics and Molecular Biology, Academic Press Inc).

Example 1

Constructing the Truncated FUR1Δ105 Gene

The EcoRI/HindIII fragment carrying the wild-type FUR1 gene is isolated from the plasmid pHX (Kern et al., 1990, Gene 88, 149-157) and inserted into the integrating yeast plasmid pRS306 (Sikorski and Hieter, 1989, Genetics 122, 19-27) which has been digested with these same enzymes, in order to form the plasmid pRS306FUR1. Starting with this latter plasmid, the FUR1 gene is recloned, in the form of a XhoI/EcoRI fragment, into the yeast centromeric plasmid pRS314 (Sikorski and Hieter, 1989, Genetics 122, 19-27), which has been treated with XhoI and EcoRI. This yields the phagemid pRS314FUR1, from which the uracil-containing single strand is prepared in the *E. coli* strain CJ236 (dut, ung, thi, relA, pCJ105 (Cm$^R$)); site-directed mutagenesis is then carried out on this strand using the Kunkel technique (Muta-Gene phagemid kit, In vitro Mutagenesis Version 2; Biorad). The aim of the mutagenesis is to introduce EcoRI and MluI restriction sites 5' of the initiating ATG and 3' of the stop codon, respectively, of the FUR1 gene and to modify the context of the initiating ATG in accordance with the Kozak rules, which entails the second Asn codon being changed into Asp. The oligonucleotides described in SID NO: 3 and NO: 4 are used to do this. The plasmid which is thereby generated, i.e. pRS314FUR1+1, is used as a control for the wild-type UPRTase activity.

In parallel, the first 105 nt of the FUR1 coding sequence are deleted by mutagenizing plasmid pRS314FUR1 using the oligonucleotides described in SID NO: .5 and NO: 4. The resulting plasmid, i.e. pRS314FUR1+106, contains the same modifications as its complete equivalent, namely an EcoRI site 5' of the ATG codon (corresponding to the Met +36 of the native protein), a Kozak consensus at this point, together with a change of the following Ser codon into Ala, and an MluI site 3' of the stop codon. The EcoRI/SacI fragment from pRS314FURI+106 is recloned into plasmid pRS314FUR1+1, which has been cleaved with EcoRI and SacI, in order to form the plasmid pRS314FUR1Δ105, which carries an FUR1 gene which expresses a protein whose first 35 N-terminal residues have been deleted.

Example 2

Complementation of an Fur1 Mutant of *S. Cerevisiae*

The functional ability of the FUR1 expression products obtained from the above constructs is assessed by the complementation of an furl-8 trpl-4 mutant of *S. cerevisiae* (Jund and Lacroute, 1970, J. Bacteriol. 102, 607-615) which has been transformed with the different plasmids of the pRS314 type. The transformants are cultured either in the conventional manner (minimal YNB medium) or in the presence of 5 mM 5-FU, and their ability to grow at 30° C. and 37° C. is evaluated. The results are presented in Table 1, where + represents growth and – represents the absence of growth, testifying to sensitivity to 5-FU and therefore to a UPRTase activity.

TABLE 1

| Transformants | YNB medium (minimal) 30° C. and 37° C. | +5 mM 5-FU 30° C. and 37° C. |
|---|---|---|
| PRS314 [sic] | + | + |
| pRS314FUR1 | + | – |
| pRS314FUR1+1 | + | – |
| pRS314FUR1+106 | + | – |
| pRS314FUR1Δ105 | + | – |

All the transformants are of course able to grow in conventional YNB medium. By contrast, only the transformant harboring the "empty" pRS314 plasmid, which does not contain the FUR1 sequences, is able to grow in the presence of 5-FU whereas those transformants which have been given the plasmids containing the native FUR1 sequences (pRS314FUR1), the FUR1 sequences which have been mutated at the level of the first ATG codon (pRS314FUR1+1), the FUR1 sequences which have been mutated at the level of the second ATG codon (pRS314FUR1+106) or the truncated FUR1 sequences (pRS314FUR1Δ105) are sensitive to the presence of 5-FU. These complementation tests demonstrate that the different constructs produce a functional UPRTase enzyme and that deleting the 35 N-terminal residues does not have any negative effect on the activity of the enzyme.

Example 3

Expressing FUR1 and FUR1Δ105 in Mammalian Cells

The EcoRI/MluI fragments of pRS314FUR1+1 and pRS314FUR1Δ105, carrying the FUR1 and FUR1Δ105 genes, were introduced into the eukaryotic expression plasmid pCI-neo (Promega) in order to form the plasmids pCI-neoFUR1+1 and pCI-neoFUR1Δ105, respectively. COS7 cells (ATCC CRL-1651) are transiently transfected with these plasmids and the UPRTase enzymic activity is determined in the cell extracts.

More precisely, 5×10⁵ COS7 cells are sown, at 37° C., in 60 mm culture dishes containing 5 ml of DMEM medium supplemented with 10% fetal calf serum (FCS). On the following day, the cells are treated with 20 µl of lipofectin (Gibco BRL) in the presence or absence of 5 µg of plasmid and culturing is continued in 2 ml of DMEM medium. After 16 hours of incubation at 37° C., the cells are replaced in 5 ml of DMEM-10% FCS for approximately 48 hours. The cells are then washed and resuspended in 30 µl of lysis buffer (50 mM Tris-HCl, pH 7.5/150 mM NaCl/5 mM EDTA/1 mM DTT/1% triton X-100) at 4° C. for 30 minutes. The cell lysate is collected and centrifuged, and the UPRTase enzymic activity is assayed on the resulting supernatant. To do this, 4 µl of lysate are incubated at 37° C. for 10 minutes in the presence of 2 µl of UPTRase reaction buffer (100 mM Tris-HCl pH 7.5/10 mM MgCl$_2$/10 mM 5-PRPP (5-phosphoribosylpyrophospate)/3 mM [C$^{14}$] uracil having 0.02 µCi/µl (NEN)). The enzyme reactions are stopped by heating at 100° C. for one minute. 1 µl aliquots are loaded onto a polyethyleneimine-cellulose TLC plate (Merck). The uracil is separated from the UMP by using water as the migration solvent. Following migration, the TLC plate is scanned with a PhosphorImager (445 SI; Molecular Dynamics). The protein concentration is measured by the Bradford method (protein Assay; Biorad). The UPRTase activity was determined on the basis of three independent transfections, and the results are shown in Table 2.

TABLE 2

| Transfected plasmid | UPRTase activity (37° C.) pmol of uracil transformed/ minute/mg of protein |
|---|---|
| — | not detectable |
| PCI-neo | not detectable |
| PCI-neoFUR1+1 | 91 +/– 15 |
| PCI-neoFUR1Δ105 | 3150 +/– 420 |

The transformation of uracil into UMP is only observed in the cells which have been transfected with the plasmids expressing a complete FUR1 gene (pCI-neoFUR1+1) or truncated FUR1 gene (pCI-neoFUR1Δ105). It is also noted that the UPRTase activity encoded by the truncated gene is higher than that encoded by the complete gene by a factor of 30.

Example 4

Constructing an Adenoviral Vector for Transferring the Truncated FUR1Δ105 Gene and Infecting Human Tumor Cells 1. Constructing pTG6289 for Expressing FUR1Δ105

The EcoRI/MluI fragment from pCI-neoFUR1Δ105, encompassing the truncated gene, is isolated and introduced into the vector pTG6600, which has been cleaved with the same enzymes, in order to form the transfer vector pTG6288. For information, pTG6600 is a p polyII vector (Lathe et al., 1987, Gene 57, 193-201) into which the Ad5 1 to 458 sequences, the early CMV promoter, the hybrid splicing sequences found in plasmid pCI (Promega Corp, comprising the splicing donor site of intron 1 of the human β-globin gene and the splicing acceptor site of the mouse immunoglobulin gene), the SV40 virus polyadenylation sequences and the Ad5 3328-5788 sequences have been inserted. Effecting such a construct is within the capacity of the skilled person, in particular on the basis of document FR-A-2 763 959. The adenoviral vector pTG6289 is reconstituted by recombination, in *E. coli* strain BJ 5183, between the PacI/BstEII fragment from pTG6288 and the ClaI-linearized vector pTG6624 (described in document FR-A-2 763 959). For information, pTG6624 corresponds to plasmid p poly II which is carrying the Ad5 genome, from which the E1 (nt 459 to 3327) and E3 (nt 28592 to 30470) regions have been deleted, together with an expression cassette, which is inserted in place of E1.

The final pTG6289 construct contains the Ad5 genome from which the bulk of the E1 (nt 459 to 3328) and E3 (nt 28249 to 30758) regions have been deleted and, in place of E1, a cassette for expressing the FUR1Δ105 gene, which is placed under control of the early CMV promoter and hybrid β-globin/Ig splicing sequences. The adenoviral particles are generated by transfecting a cell line which complements the E1 function, for example the 293 cell line (ATCC CRL1573) in accordance with the techniques of the art (Graham and Prevec, 1991, Methods in Molecular Biology Vol. 7, Gene Transfer and Expression Protocols; Ed. E. J. Murray, The Human Press Inc, Clinton, N.J.).

2. Constructing a Vector for Expressing the FCY1 Gene

The uracil-containing single strand is isolated from the expression phagemid pRS315FCY1 (Erbs et al., 1997, Curr. Genet. 31, 1-6), which strand is modified by means of site-directed mutagenesis (Muta-gene Phagemid kit, In vitro Mutagenesis version 2; Biorad). The mutagenesis uses the oligonucleotides of SID NO: 6 and NO: 7, making it possible to introduce a HindIII site 5' of the initiating ATG, and an EcoRI site 3' of the stop codon, of the FCY1 gene and to modify the translational context in accordance with the Kozak rules. The HindIII/EcoRI fragment, which has been modified in this way, is inserted into the plasmid pRS306 (Sikorski and Hieter, 1989, Genetics 122, 19-27), which has been digested with the same enzymes, in order to form pRS306FCY1. The XhoI/XbaI fragment from pRS306FCY1 is subcloned into the vector pCI-neo (Promega), which has been cleaved with XhoI and XbaI. This results in pcI-neoFCY1 comprising the FCY1 gene having a Kozak consensus sequence at the level of its intiating ATG.

An adenoviral vector for expressing the S. cerevisiae FCY1 gene, encoding the enzyme CDase, is generated. The XhoI/XbaI fragment from plasmid pCI-neoFCY1, encompassing the FCY1 gene, is introduced into the XhoI-XbaI-digested vector pTG6600 in order to form pTG6286. As before, homologous recombination between the PacI/BstEII fragment, which carries FCY1 and which was isolated from pTG6286, and the ClaI-linearized vector pTG6624 generates the adenoviral vector pTG6287, which is deleted for the E1 and E3 regions and which contains the FCY1 gene, instead of E1, placed under the control of the CMV promoter and hybrid β-globin/Ig splicing sequences. The viral particles (AdTG6287) are obtained by transfecting 293 cells.

3. Determining the Enzyme Activities

The adenoviral constructs are tested on three human tumor cell lines: PANC-1 (pancreatic carcinoma/ATCC CRL-1469), SK-BR-3 (breast adenocarcinoma/ATCC HTB-30) and SW480 (colon adenocarcinoma/ATCC CCL-228). These cells were chosen because of their resistance to 5-FU, thereby making it possible to determine the efficacy of the FUR1Δ105 gene.

More precisely, 5×106 cells suspended in 100 μl of PBS-2% FCS are incubated at 37° C. for 30 minutes in the presence of the adenoviruses to be tested (Ad.CMV-FCY1 and Ad.CMV-FUR1, or a mixture of the two) at an MOI (multiplicity of infection) of 20. As a negative control, either a mock infection is carried out or an infection is carried out with a first-generation adenovirus which lacks the gene of interest (Ad null). The infected cells are taken up in 500 μl of DMEM-10% FCS and placed in a 35 mm culture dish at a rate of $1\times10^6$ cells per dish. After 48 hours of incubation at 37° C., the different enzymic activities, using 5-FC or 5-FU as a substrate, are determined on the cell lysates. The UPRTase activity is measured, in accordance with the abovedescribed protocol, on 4 μl of cell lysate, which are incubated at 37° C. for 20 minutes in the presence of 2 μl of UPRTase reaction buffer ([$C^{14}$] 5-FU, Sigma). In the case of the CDase activity, use is made of 4 μl of cell lysate, which are incubated at 37° C. for 20 min together with 2 μl of CDase reaction buffer (100 mM Tris-HCl, pH 7.5/3 mM [$H^3$] 5-FC, having 0.25 μCi/μl, Sigma). The conversion of 5-FC into 5-FUMP (CDase/UPRTase activities) is determined on 4 μl of cell lysate which are incubated at 37° C. for 20 min in the presence of 2 μl of CDase/UPRTase reaction buffer (100 mM Tris-HCl, PH 7.5/10 mM $MgCl_2$/10 mM 5-PRPP/3 mM [$H^3$] 5-FC having 0.25 μCi/μl). 1 μl aliquots are loaded onto a PEI cellulose TLC plate. The 5-FU is separated from the 5-FC by using water as the solvent, and the 5-FUMP is separated from the 5-FU by using a water/1-butanol (14%/86%) mixture as the solvent.

In the three cell types, CDase activity is observed in the extracts obtained from the cells which were infected with the adenovirus expressing the FCY1 gene (Ad.CMV-FCY1) and from the cells which were coinfected with the two viruses, i.e. Ad.CMV-FCY1 and Ad.CMV-FUR1Δ105. The enzyme assay shows a varying activity of from about 80 to 100 pmol of 5-FC transformed/min/mg of protein in the PANC-1, SK-BR3 and SW480 cells. As far as the transformation of the 5-FU is concerned (UPRTase activity), an endogenous activity of approximately some one hundred pmol of 5-FU transformed/min/mg of protein is observed. The activity is amplified by a factor of 7 to 8 when the infection is carried out with the Ad.CMV-FUR1Δ5 adenovirus on its own or when the cells-are coinfected. Finally, the conversion of 5-FC to 5-FUMP is detected in the extracts which have been infected with Ad-CMV-FCY1 (due to the endogenous UPRTase activity) and when the cells are coinfected.

In addition, the $LD_{50}$ (50% lethal dose) values of 5-FC and 5-FU (μM) are determined with regard to the three human tumor cell lines which are infected with the above viruses (Mock infection, Ad null infection, Ad.CMV-FCY1 infection and Ad.CMV-FUR1Δ105 infection) or which are coinfected with the adenoviruses expressing the FCY1 and FUR1Δ105 genes. The cells are infected at an MOI of 20 and then cultured in the presence or absence of drugs (5-FC or 5-FU) at various concentrations. Trypan blue is added after trypsinizing on D+6. The living cells do not take up trypan blue while the dead cells are stained. The % mortality. is assessed under the microscope. The values reported below are the means obtained after four counts.

The $LD_{50}$ of the infected cell lines with regard to 5-FC is between 5 and 10 μM (depending on the cell lines) when the two FCY1 and FUR1Δ105 genes are coexpressed, whereas it is from 100 to 500 μM when the FCY1 gene is expressed on its own and from 5000 to 10,000 μM in the case of the negative controls (Mock infection and Ad null infection) and in the case of Ad.CMV-FUR1Δ105. In the same way, the $LD_{50}$ with regard to 5-FU is considerably lower when the infection uses the virus expressing the FUR1Δ105 gene as compared with the negative controls and in the infection using Ad.CMV-FCY1 on its own. These results demonstrate the importance of using the synergistic effect of the FCY1 and FUR1Δ105 genes in a "suicide" gene approach for improving conversion of the 5-FC prodrug into cytotoxic 5-FUMP.

Example 5

Constructing a Hybrid Gene Which Encodes a Fusion Protein Carrying the CDase and UPRTase Activities 1. Constructing the Gene Fusion The EcoRI/NotI fragment from pCI-neoFUR1Δ105 is inserted into the EcoRI/NotI-cut plasmid pCI-neoFCY1 in order to give the plasmid pCI-neoFCY1+FUR1Δ105. Using this uracil-containing single-stranded plasmid as the starting point, the FCY1 and FUR1Δ105 are fused by means of site-directed mutagenesis using the oligonucleotide OTG 11615 (SID NO: 8). The modification consists in deleting the stop codon of FCY1 and the initiating Met codon of FUR1, thereby enabling the FCY1 and FUR1Δ105 sequences to be fused in-phase without any spacer (this fusion is designated FCU1 below).

2. Enzymic Characterization of the Bifunctional FCU1 Protein

The previously described techniques are used to determine the CDase and UPRTase activities (10 minute reaction at 37° C.) in cell lysates from COS7 cells which were:

untransfected transfected with 10 µg of pCI-neo (empty plasmid)

transfected with 5 µg of pCI-neoFCY1+5 µg of pCI-neoFUR1Δ105 transfected with 5 µg of pCI-neo+5 µg of pCI-neoFCU1

The values obtained are listed in Table 3 below and are the means of three enzyme determinations.

TABLE 3

| COS7 | CDase pmol of cytosine transformed/min/ mg of protein | UPRTase pmol of uracil transformed/min/ mg of protein | CDase/ UPRTase pmol of UMP formed/min/mg of protein |
|---|---|---|---|
| Untransfected | not detectable | not detectable | not detectable |
| pCI-neo | not detectable | not detectable | not detectable |
| PCI-neoFCY1 + PCI-neoFUR1Δ105 | 626 +/− 106 | 3005 +/− 298 | 535 +/− 54 |
| pCI-neo + pCI-neoFCU1 | 5373 +/− 268 | 2789 +/− 310 | 2121 +/− 107 |

An equivalent UPRTase activity is observed whether the gene is in the fused form (pCI-neoFCU1) or in the unfused form (pCI-neoFUR1Δ105). Surprisingly, the CDase activity is increased by a factor of 10 when the gene is in the fused form as compared with the unfused FCY1 gene. Thus, the fused form is beneficial since it gives rise to an increase in the aggregate CDase-UPRTase activity and therefore to an increase in the formation of 5-FUMP from 5-FC.

The UPRTase activity of the fusion protein encoded by FCU1 is limiting in relation to the CDase activity; the formation of a pool of uracil of the order of 3000 pmol of uracil/min/mg of protein is detected in vitro during the CDase-UPRTase reaction. This pool of uracil does not exist under the same conditions when the reaction makes use of the FCY1 and FUR1Δ105 proteins.

3. Expressing the FCY1, FUR1Δ105 and FCU1 Genes, Which have Been Cloned into the Plasmid pCI-neo, in B16 (F0) Cell Lines The efficiency of the FCU1 gene fusion is assessed by transfecting the B16(F0) mouse melanoma cell line (ATCC CRL-6322). In order to do this, $2.5 \times 10^5$ B16(F0) cells are seeded, at 37° C., in 60 mm dishes containing 5 ml of DMEM-10% FCS medium. After 48 hours of incubation, the cells were treated with 20 µl of lipofectin (Gibco BRL) in the presence of 5 µg of plasmid and culturing was then continued at 37° C. for 16 hours in 2 ml of DMEM medium. 48 hours after that, the cells are placed in 5 ml of DMEM-10% FCS and then diluted, in 10 cm Petri dishes, in DMEM-10% FCS medium containing 1 mg of G418/ml. Clones which are resistant to G418 are visible after 20 days. The clones obtained for each construct are collected, transferred into T150 flasks and cultured in selective medium. The CDase, UPRTase and CDase-UPRTase activities are determined at 37° C. in the presence of 5-FC or 5-FU as the substrate. The values shown are the means obtained after three enzyme determinations (see Table 4).

TABLE 4

| B16(F0) | CDase pmol of 5-FC transformed/min/ mg of protein | UPRTase pmol of 5-FU tranformed/min/ mg of protein | CDase/UPRTase pmol of 5-FUMP formed/min/mg of protein |
|---|---|---|---|
| Untransfected | not detectable | 310 +/− 77 | not detectable |
| pCI-neo | not detectable | 238 +/− 56 | not detectable |
| pCI-neoFCY1 | 3 +/− 0.4 | 292 +/− 93 | 2 +/− 0.4 |
| pCI-neoFUR1Δ105 | not detectable | 813 +/− 47 | not detectable |
| pCI-neoFCU1 | 158 +/− 9 | 834 +/− 67 | 41 +/− 5 |

The enzyme results confirm those determined using transfected COS7 cells, namely a conserved UPRTase activity but a CDase activity which is strongly increased in the case of the fusion protein as compared with that measured using the native FCY1 protein. In the case of the B16 clones transfected with pCI-neoFCU1, a pool of 5-FU (120 pmol/min/mg of protein), which is the consequence of the increase in the CDase activity, also appears in vitro.

The sensitivities of the different clones to 5-FC and 5-FU are also tested after incubating in the presence of the drugs for 6 days. The following values are the means of four counts (using trypan blue) of cell mortality. The $LD_{50}$ for 5-FC is 10 µM in the case of the cells transfected with the plasmid carrying the (pCI-neoFCU1) gene fusion as compared with 100 µM when using pCI-neoFCY1 and 1000 µM when using the negative controls (untransfected cells and cells transfected with pCI-neo) and when using pCI-neoFUR1A1Δ105. The $LD_{50}$ for 5-FU is 0.03 µM when the transfection is carried out using pCI-neoFUR1Δ105 or pCI-neoFCU1 as against 0.05 µM in all the other cases.

These results demonstrate that the expression of the FCU1 gene sensitizes the cells to 5-FC more strongly than does the expression of the FCY1 gene. This difference in sensitization to 5-FC is due to the fusion protein having a higher CDase activity and not to the presence of the UPRTase activity; this UPRTase activity, which is encoded by the S. cerevisiae gene, has little effect on the toxicity of the 5-FU for the B16(F0) cells, which are naturally very sensitive to 5-FU and which exhibit substantial endogenous UPRTase activity.

4. Demonstrating that B16(F0) Cells Which Are Transfected With the FCU1 Gene Exhibit a Bystander Effect The appearance of a pool of 5-FU in the in vitro assay of the CDase-UPRTase activity of the FCU1-transfected B16(F0) cells is, a priori, an advantage for potentiating the bystander effect: the greater the size of this intracellular pool, the greater will be the passive diffusion of the 5-FU in the medium and the greater will be the mortality of the untransfected cells.

In order to demonstrate this bystander effect, untransfected B16(F0) clones were mixed, in different proportions, with B16(F0) clones which were transfected with pCI-neoFCU1. These clone mixtures were then tested in the presence of different concentrations of 5-FC. Cell mortality (using trypan blue) is assessed after culturing for 4 days in the presence of 5-FC. The results (means of 4 determinations) are presented in Table 5 below.

TABLE 5

| B16/B16 pCI-neoFCU1 in % | $LD_{50}$ (µM) + 5-FC |
|---|---|
| 100%/0% | 5000 |
| 95%/5% | 500 |

TABLE 5-continued

| B16/B16 pCI-neoFCU1 in % | $LD_{50}$ (µM) + 5-FC |
|---|---|
| 90%/10% | 300 |
| 75%/25% | 200 |
| 50%/50% | 100 |
| 0%/100% | 50 |

It is seen that the $LD_{50}$ for 5-FC is lowered by a factor of 10 as soon as the cell mixture contains 5% of FCU1-transfected cells, thereby testifying to the existence of a bystander effect. The $LD_{50}$ does of course continue to decrease when the proportion of transfected cells increases.

With the aim of demonstrating that this bystander effect does not, contrary to the tk/ganciclovir system, require any contact between the cells, due to the diffusion of the 5-FU into the medium, (untransfected) B16 cells were incubated for 4 days in medium (diluted one to four in new medium) which was derived from the culture supernatants from B16 (negative control) or B16 pCI-neoFCU1 clones which have been incubated for 48 hours in the presence of different concentrations of 5-FC, and the mortality of the B16 cells was assessed using trypan blue. The results demonstrate a drastic effect on the $LD_{50}$ and show that 5-FU is present in the medium as the consequence of the protein fusion encoded by the FCU1 gene having a high CDase activity.

Example 6

Constructing an Adenoviral Vector for Transferring the FCU1 Gene and Infecting Tumor Cells 1. Constructing pTG13060 for Expressing FCU1

The XhoI/MluI fragment from pCI-neoFCU1, encompassing the FCU1 gene fusion, is isolated and introduced into the XhoI/MluI-linearized vector pTG6600 in order to form the transfer vector pTG13059. Homologous recombination between the PacI/BstEII fragment, which carries FCU1 and which is isolated from pTG13059, and the ClaI-linearized vector pTG6624 generates the adenoviral vector pTG13060, which is deleted for the E1 and E3 regions and which contains, in the place of E1, the FCU1 gene placed under the control of the CMV promoter and hybrid β-globin/Ig splicing sequences. The viral particles (Ad.CMV-FCU1) are obtained by transfecting 293 cells.

2. Expressing the FCU1 Gene, Which is Cloned in an Adenoviral Vector, in Tumor Cells The new adenoviral construct is tested on three human tumor cell lines: PANC-1, SK-BR-3 and SW480. The above-described techniques are used to determine the CDase and UPRTase activities (employing 5-FC or 5-FU as the substrate) in cell lysates obtained from the human cells, which were infected at an MOI of 20. A UPRTase activity (of from 700 to 800 pmol of 5-FU transformed/min/mg of protein) is observed in the three cell lines infected with Ad.CMV-FCU1 which is equivalent to the UPRTase activity expressed by the FUR1Δ105 gene. In the three cell types, the CDase activity is amplified by a factor of 100 (10,000 to 12,000 pmol of 5-FC transform/min/mg of protein) when the gene is expressed in fusion form (FCU1) as compared with the activity of the cells when infected with Ad.CMV-FCY1.

When expressed from an adenoviral vector, the fusion protein exhibits a UPRTase activity, as in Example 5, which is limiting in relation to the CDase activity and which leads to the formation of a substantial pool of 5-FU of the order of 10,000 pmol of 5-FU/min/mg of protein during the CDase-UPRTase reaction. This accumulation of 5-FU potentiates the bystander effect.

The $LD_{50}$ values for 5-FC and 5-FU are determined vis-a-vis the three human tumor cell lines infected with the different viruses (Ad null, Ad.CMV-FCY1, Ad.CMV-FUR1A1Δ105 and Ad.CMV-FCU1) or coinfected with the adenoviruses expressing the FCY1 and FUR1Δ105 genes. The cells are infected at an MOI of 5 and then cultured in the presence of different concentrations of 5-FC and 5-FU. After 6 days of culture, the viability of the cells is determined using trypan blue. The $LD_{50}$ values listed in Table 6 are the means of four counts.

TABLE 6

|  |  | $LD_{50}$ (µM) 5-FU | $LD_{50}$ (µM) 5-FC |
|---|---|---|---|
| PANC-1 | Mock | 0.3 | 10,000 |
|  | Ad null | 0.3 | 10,000 |
|  | Ad.CMV-FCY1 | 0.3 | 500 |
|  | Ad.CMV-FUR1Δ105 | 0.01 | 10,000 |
|  | Ad.CMV-FCY1 + Ad.CMV-FUR1Δ105 | 0.01 | 20 |
|  | Ad.CMV-FCU1 | 0.01 | 0.5 |
| SK-BR-3 | Mock | 0.1 | 5000 |
|  | Ad null | 0.1 | 5000 |
|  | Ad.CMV-FCY1 | 0.1 | 300 |
|  | Ad.CMV-FUR1Δ105 | 0.005 | 5000 |
|  | Ad.CMV-FCY1 + Ad.CMV-FUR1Δ105 | 0.005 | 10 |
|  | Ad.CMV-FCU1 | 0.005 | 0.03 |
| SW480 | Mock | 0.5 | 5000 |
|  | Ad null | 0.5 | 5000 |
|  | Ad.CMV-FCY1 | 0.5 | 300 |
|  | Ad.CMV-FUR1Δ105 | 0.03 | 5000 |
|  | Ad.CMV-FCY1 + Ad.CMV-FUR1Δ105 | 0.03 | 20 |
|  | Ad.CMV-FCU1 | 0.03 | 0.3 |

These results demonstrate that expression of the FCU1 gene from an adenoviral vector sensitizes the cells to 5-FC more strongly than does the coexpression of the FCY1 and FUR1Δ105 genes. This greater sensitivity to 5-FC results from the increase in the CDase activity encoded by the FCU1 gene fusion.

3. Demonstrating That Human Tumor Cells Infected with the Different Adenoviruses Exhibit a Bystander Effect The human tumor cells PANC-1, SK-BR-3 and SW480 are infected (Ad null, Ad.CMV-FCY1, Ad.CMV-FUR1Δ105 and Ad.CMV-FCU1) at an MOI of 20. After 48 hours of incubation at 37° C., the cells are rinsed twice with PBS, trypsinized and spread out, in different proportions, in the presence of uninfected cells. After 6 days of culturing in the presence of 1 mM 5-FC, cell mortality is assessed using trypan blue. The results (mean of 4 determinations) show that, in the case of the three tumor strains, a mixture of 10% of cells infected with Ad.CMV-FCY1 and 90% of uninfected cells leads to 100% mortality. When the cells are infected with Ad.CMV-FCU1, 1% of infected cells is sufficient to lead to 100% mortality. This experiment demonstrates the existence of a substantial bystander effect, which results from the increase in the pool of 5-FU in the cells expressing the fusion protein.

With the aim of demonstrating the secretion of 5-FU into the medium by cells expressing FCY1 and FCU1 in the presence of 5-FC, $10^6$ PANC-1, SK-BR-3 and SW480 cells are infected (Ad null, Ad.CMV-FCY1, Ad.CMV-FUR1Δ105 and Ad.CMV-FCU1) at an MOI of 20. The cells are cultured in the presence of 1 mM [$^3$H]5-FC, giving 0.25 µCi/µl. After 48 hours of culture, 2 µl aliquots of culture medium are loaded onto a cellulose TLC plate. The 5-FU is separated from the 5-FC by using a water/1-butanol (14%/86%) mixture as the solvent. In the three cell types, approximately 20% of the 5-FC is converted into 5-FU when the cells are infected with Ad.CMV-FCY1. More than 90% of the 5-FC is transformed into 5-FU when the cells are infected with Ad.CMV-FCU1.

4. Comparing the Efficacy of the FCU1/5-FC and TK/GCV Systems

With the aim of comparing the efficiency of the FCU1/5-FC system in relation to the TK/GCV system, an adenoviral vector is generated for expressing the herpes simplex virus type 1 thymidine kinase gene (HSV-1 TK). The EcoRI/XbaI fragment from pTG4043, encompassing the HIV-1 TK CDNA, is isolated and introduced into the EcoRI/XbaI-linearized vector pTG6600, in order to form the transfer vector pTG6222. Homologous recombination between the PacI/BstEII fragment, which carries HSV-1 TK and which is isolated from pTG6222, and the ClaI-linearized vector pTG6624 generates the adenoviral vector pTG13019, which is deleted for the E1 and E3 regions and which contains, in the place of E1, the HSV-1 TK gene placed under the control of the CMV promoter and hybrid β-globin/Ig splicing sequences. The viral particles (Ad.CMV-TK) are obtained by transfecting 293 cells.

The human cells PANC-1, SK-BR-3 and SW480, and also the murine cells B16(F0) and RENCA (renal carcinoma, Murphy et al. J. Natl Cancer Inst., 1973, 50(4): 1013-25) are infected with Ad null, Ad.CMV-FCU1 or Ad.CMV-TK. The cells are cultured in the presence of different concentrations of 5-FC or GCV. After 10 days of culture, the viability of the cells is determined by counting with trypan blue. The therapeutic index (Table 7) corresponds to the $LD_{50}$ of the uninfected cells (or $LD_{50}$ of the cells infected with Ad null)/$LD_{50}$ of the cells infected with Ad.CMV-FCU1 or with Ad.CMV-TK ratio. The therapeutic index of the FCU1/5-FC system is generally higher than that of the TK/GCV system, indicating that the suicide gene strategy based on the FCU1/5-FC combination is more therapeutically efficacious.

TABLE 7

| | FCU1/5-FC therapeutic index | TK/GCV therapeutic index |
|---|---|---|
| B16(F0) MOI 50 | 30 | 10 |
| RENCA MOI 5 | 100 | 100 |
| SW480 MOI 1 | 300 | 100 |
| PANC-1 MOI 1 | 1000 | 150 |
| SK-BR-3 MOI 1 | 3000 | 1000 |

5. In Vivo Experiments

In order to assess the ability of the FCU1/5-FC and TK/GCV systems to inhibit the growth of tumors in vivo, $3 \times 10^5$ B16(F0) cells are injected subcutaneously into 6 groups of n=10 immunocompetent B6D2 mice (=D0). As soon as the tumors become palpable (D+8), a "vehicle" buffer (10 mM Tris, pH 8, 1 mM $MgCl_2$) or the adenoviruses (see the legend to FIGS. 1 and 2), which are resuspended in this same buffer, are injected at a dose of $5 \times 10^8$ IU by the intratumor route, on three occasions (D+8, D+9 and D+10). From D+8 onwards, 1 ml of a 0.9% saline solution, or 1 ml of a 1% solution of 5-FC or 1 ml of a 0.1% solution of GCV is injected intraperitoneally twice a day up to D+43. The results (FIG. 1 and FIG. 2) show an increase in survival in the group injected with Ad.CMV-FCU1 and treated with 5-FC as compared with the Ad.CMV-TK group which is treated with GCV and with the control groups. These results confirm the value of combining the FCU1 gene and the 5-FC prodrug, in particular when implementing an antineoplastic treatment.

Example 7

Combining the FCU1 Suicide Gene and Genes Encoding Cytokines

The combination of FCU1 and cytokines (IFNγ and IL-2) is tested in vivo in the murine tumor model in which B16(F0) cells are implanted in immunocompetent B6D2 mice. The adenoviruses encoding the cytokines are Ad.CMV-muIFNγ (AdTG13048), which expresses murine IFNγ, and Ad.CMV-HuIL-2 (AdTG6624) which expresses human IL-2.

The vector pTG13048, for expressing murine IFNγ, was constructed in the following manner: The SalI/NotI fragment from pTG8390, encompassing the cDNA for murine IFNγ (muIFNγ), is isolated and introduced into the XhoI/NotI-linearized vector pTG6600 in order to form the transfer vector pTG13047. Homologous recombination between the PacI/BstEII fragment, which carries muIFNγ and which is isolated from pTG13047, and the ClaI-linearized vector pTG6624 generates the adenoviral vector pTG13048, which is deleted for the E1 and E3 regions and which contains, in place of E1, the muIFNγ gene placed under the control of the CMV promoter and hyrid β-globin/Ig splicing sequences. The viral particles (Ad.CMV-muIFNγ) are obtained by transfecting 293 cells. The pTG6624 vector, expressing human IL-2, is described in the document FR-A-2 763 959.

$3 \times 10^5$ B16(F0) cells are injected subcutaneously into 10 groups of 13 immunocompetent B6D2 mice (=D0). As soon as the tumors become palpable (D=7), a "vehicle" buffer' (10 mM Tris, pH 8, 1 mM $MgCl_2$) or the adenoviruses, or a combination of adenoviruses (see the legend to FIGS. 3 and 4), which are resuspended in this same buffer, are injected at a dose of $2 \times 10^8$ IU per adenovirus ($4 \times 10^8$ IU in total), by the intratumor route, on three occasions (D+7, D+8 and D+9). From D+7 onwards, 1 ml of an 0.9% saline solution or 1 ml of a 1% solution of 5-FC are injected intraperitoneally twice a day. The survival curves (FIG. 3 and FIG. 4) show that synergy exists between the suicide gene and the cytokine which is included in the composition of the invention. This synergy is illustrated by a rate of survival which is higher in the case of the FCU1/cytokine combinations as compared with the approach which consists in using an adenovirus encoding the suicide gene on its own or using a cytokine on its own.

The invention claimed is:

1. A method for treating cancer of the central nervous system, the method comprising:
   administering, to an organism in need of treatment, a recombinant modified vaccinia virus Ankara (MVA) expression vector comprising
   a promoter operably-linked to a nucleotide sequence encoding a fusion protein comprising
      a CDase that exhibits cytosine deaminase activity at a higher level than that of a native CDase, wherein the CDase comprises the amino acid sequence of SEQ ID NO: 2; and
      a mutant UPRTase that exhibits uracil phosphoribosyltransferase activity at a higher level than that of a native UPRTase, wherein the mutant UPRTase comprises the amino acid sequence of SEQ ID NO: 1;
   wherein the recombinant modified vaccinia virus Ankara (MVA) expression vector is intratumorally administered.

2. The method of claim 1, wherein the mutant UPRTase exhibits a level of uracil phosphoribosyltransferase activity higher than the native UPRTase by a factor from about 2 to 100.

3. The method of claim 1, wherein the mutant UPRTase exhibits a level of uracil phosphoribosyltransferase activity higher than the native UPRTase by a factor from about 5 to 75.

4. The method of claim 1, wherein the mutant UPRTase exhibits a level of uracil phosphoribosyltransferase activity higher than the native UPRTase by a factor from about 10 to 50.

5. The method of claim 1, wherein the CDase is fused with the N-terminal end of the mutant UPRTase.

6. The method of claim 1, wherein the fusion protein increases the sensitization of target cells to 5-FC by at least a factor of 2, at least a factor of 5, and/or at least a factor of 10.

7. The method of claim 1 further comprising:
   administering a pharmaceutically acceptable quantities of a prodrug selected from the group consisting of a cytosine analog and 5-FC.

* * * * *